US008158374B1

(12) United States Patent
He et al.

(10) Patent No.: US 8,158,374 B1
(45) Date of Patent: Apr. 17, 2012

(54) QUANTITATIVE DIAGNOSTIC METHODS USING MULTIPLE PARAMETERS

(75) Inventors: Yiwu He, Cary, NC (US); Bo Pi, Carlsbad, CA (US); John Bilello, Durham, NC (US)

(73) Assignee: Ridge Diagnostics, Inc., San Diego, CA (US)

(*) Notice: Subject to any disclaimer, the term of this patent is extended or adjusted under 35 U.S.C. 154(b) by 160 days.

(21) Appl. No.: 11/850,550

(22) Filed: Sep. 5, 2007
(Under 37 CFR 1.47)

Related U.S. Application Data

(60) Provisional application No. 60/910,217, filed on Apr. 5, 2007, provisional application No. 60/824,471, filed on Sep. 5, 2006.

(51) Int. Cl.
*G01N 33/53* (2006.01)
*G01N 33/537* (2006.01)
*G01N 33/567* (2006.01)
*G01N 33/566* (2006.01)

(52) U.S. Cl. ........ 435/7.92; 435/7.1; 435/7.21; 435/7.8; 436/501; 436/503

(58) Field of Classification Search .................. None
See application file for complete search history.

(56) References Cited

U.S. PATENT DOCUMENTS

| | | | |
|---|---|---|---|
| 5,647,030 | A | 7/1997 | Jorgenson et al. |
| 5,658,802 | A | 8/1997 | Hayes et al. |
| 5,804,453 | A | 9/1998 | Chen |
| 5,882,203 | A | 3/1999 | Correa et al. |
| 7,041,206 | B2 | 5/2006 | Gephart et al. |
| 7,094,595 | B2 | 8/2006 | Cunningham et al. |
| 7,136,518 | B2 | 11/2006 | Griffin et al. |
| 2001/0045355 | A1 | 11/2001 | Gephart et al. |
| 2002/0095073 | A1 | 7/2002 | Jacobs et al. |
| 2003/0016360 | A1 | 1/2003 | Chase et al. |
| 2003/0032773 | A1 | 2/2003 | Herath et al. |
| 2003/0109420 | A1 | 6/2003 | Valkirs et al. |
| 2004/0110938 | A1 | 6/2004 | Parekh et al. |
| 2004/0117212 | A1 | 6/2004 | Kong et al. |
| 2004/0228765 | A1 | 11/2004 | Witty et al. |
| 2004/0228766 | A1 | 11/2004 | Witty et al. |
| 2005/0069936 | A1 | 3/2005 | Diamond et al. |
| 2005/0095646 | A1 | 5/2005 | Sherman |
| 2005/0191694 | A1 | 9/2005 | Jacobs et al. |
| 2005/0239110 | A1 | 10/2005 | Rokutan et al. |
| 2005/0254062 | A1 | 11/2005 | Tan et al. |
| 2005/0254065 | A1 | 11/2005 | Stokowski |
| 2006/0019313 | A1 | 1/2006 | Andersson et al. |
| 2006/0063199 | A1 | 3/2006 | Elgebaly et al. |
| 2006/0154320 | A1 | 7/2006 | Zuk et al. |
| 2007/0059204 | A1 | 3/2007 | Witty et al. |
| 2007/0092888 | A1 | 4/2007 | Diamond et al. |
| 2007/0161042 | A1 | 7/2007 | Zuk et al. |
| 2010/0100333 | A1 | 4/2010 | Pi et al. |
| 2010/0136700 | A1 | 6/2010 | Bilello et al. |

FOREIGN PATENT DOCUMENTS

| | | |
|---|---|---|
| JP | 2004/208547 | 7/2004 |
| WO | 2007/058986 | 5/2007 |
| WO | WO 2007/067819 | 6/2007 |
| WO | 2009/111595 | 9/2009 |
| WO | 2009/114627 | 9/2009 |

OTHER PUBLICATIONS

Pavon et al., 2003, Soc. for Neurosci., Abstract No. 829.1.*
Fujita et al., 2003, J. Surgical Res., 114, pp. 90-94.*
Karege et al., 2005, Biol. Psychiatry, 57, pp. 1068-1072.*
U.S. Appl. No. 60/824,471, filed Sep. 5, 2006.
U.S. Appl. No. 60/910,217, filed Apr. 5, 2007.
Andreassen and Vestbo, "Chronic obstructive pulmonary disease as a systemic disease: an epidemiological perspective," *Eur. Respir. J.*, 2003, 22(Suppl. 46):2s-4s.
Anthonisen et al., "Hospitalizations and Mortality in the Lung Health Study," *Am. J. Respir. Crit. Care Med.*, 2002, 166:333-339.
Ashton et al., "In-patient workload in medical specialties: 2. Profiles of individual diagnoses from linked statistics," *Q. J. Med.*, 1995, 88:661-672.
Barańczyk-Kuźma et al., "Tricyclic antidepressants as inhibitors of brain glutathione-S-transferase," *Pol. Merk. Lek.*, 2001, 11:472-475 (includes English summary).
Bluthé et al., "Central injection of interleukin-13 potentiates LPS-induced sickness behavior in rats," *Neuroreport*, 2001, 12(18):3979-3983.
Camilli et al., "Death Certificate Reporting of Confirmed Airways Obstructive Disease," *Am. J. Epidemiol.*, 1991, 133(8):795-800.
Celli et al., "The Body-Mass Index, Airflow Obstruction, Dyspnea, and Exercise Capacity Index in Chronic Obstructive Pulmonary Disease," *N. Engl. J. Med.*, 2004, 350(10):1005-1012.
Donaldson et al., "Relationship between exacerbation frequency and lung function decline in chronic obstructive pulmonary disease," *Thorax*, 2002, 57:847-852.
Drew and Hen, "Adult Hippocampal Neurogenesis as Target for the Treatment of Depression," *CNS Neurol. Disord. Drug Targets*, 2007, 6:205-218.
Engström et al., "Occurrence and Prognostic Significance of Ventricular Arrhythmia is Related to Pulmonary Function. A Study From "Men Born in 1914," Malmö, Sweden," *Circulation*, 2001, 103:3086-3091.
Gil et al., "Serotonin transport is modulated differently by tetanus toxin and growth factors," *Neurochem. Int.*, 2003, 42:535-542.
Hole et al., "Impaired lung function and mortality risk in men and women: findings from the Renfrew and Paisley prospective population study," *Brit. Med. J.*, 1996, 313:711-715.
Hurst et al., "Use of Plasma Biomarkers at Exacerbation of Chronic Obstructive Pulmonary Disease," *Am. J. Respir. Crit. Care Med.*, 2006, 174:867-874.
Kim et al., "Low plasma BDNF is associated with suicidal behavior in major depression," *Prog. Neuro-psychopharmacol. Biol. Psychiatry*, 2007, 31:78-85.
Kubota et al., " Interleukin-15 and interleukin-2 enhance non-REM sleep in rabbits," *Am. J. Physiol. Regul. Integr. Comp. Physiol.*, 2001, 281:R1004-R1012.

(Continued)

*Primary Examiner* — Olga N Chernyshev
(74) *Attorney, Agent, or Firm* — Fish & Richardson P.C.

(57) ABSTRACT

Materials and Methods related to diagnosing a clinical condition in a subject, or determining the subject's predisposition to develop the clinical condition, using a multi-parameter system to measure a plurality of parameters and an algorithm to determine a disease score.

5 Claims, 27 Drawing Sheets

OTHER PUBLICATIONS

Luo et al., "RANTES Stimulates Inflammatory Cascades and Receptor Modulation in Murine Astrocytes," *Glia*, 2002, 39:19-30.

Maes, "Major depression and activation of the inflammatory response system," *Adv. Exp. Med. Biol.*, 1999, 461:25-46.

Maes et al., "Higher $\alpha_1$-antitrypsin, haptoglobin, ceruloplasmin and lower retinol binding protein plasma levels during depression: Further evidence for the existence of an inflammatory response during that illness," *J. Affect. Disord.*, 1992, 24:183-192.

Mannino et al., "Low Lung Function and Incident Lung Cancer in the United States. Data From the First National Health and Nutrition Examination Survey Follow-up," *Arch. Intern. Med.*, 2003, 163:1475-1480.

Marano et al., "Increased Plasma Concentration of Brain-Derived Neurotrophic Factor With Electroconvulsive Therapy: A Pilot Study in Patients With Major Depression," *J. Clin. Phsychiatry*, 2007, 68:512-517.

Marques-Deak et al., "Cytokine profiles in women with different subtypes of major depressive disorder," *J. Psychiatr. Res.*, 2007, 41:152-159.

Michaelson et al., "Interleukin-7 is Trophic for Embryonic Neurons and is Expressed in Developing Brain," *Dev. Biol.*, 1996, 179:251-263.

Mischoulon and Fava, "Docosahexanoic acid and ω-3 fatty acids in depression," *Psychiatr. Clin. North Am.*, 2000, 23(4):785-794.

Nissen, "Proteolytic modification of $\beta_2$-microglobulin in human serum," *Danish Med. Bul.*, 1993, 40:56-64.

Notkins, "New Predictors of Disease," *Sci. Amer.*, 2007, 71:72-79.

O'Brien et al., "Plasma cytokine profiles in depressed patients who fail to respond to selective serotonin reuptake inhibitor therapy," *J. Psychiatr. Res.*, 2007, 41:326-331.

Panagiotakos et al., "Inflammation, coagulation, and depressive symptomatology in cardiovascular disease-free people; The ATTICA study," *Eur. Heart J.*, 2004, 25:492-499.

Pauwels et al., "Global Strategy for the Diagnosis, Management, and Prevention of Chronic Obstructive Pulmonary Disease. NHLBI/WHO Global Initiative for Chronic Obstructive Lung Disease (GOLD) Workshop Summary," *Am. J. Respir. Crit. Care Med.*, 2001, 163:1256-1276.

Pavón et al., "Th2 cytokine response in Major Depressive Disorder patients before treatment," *J. Neuroimmunol.*, 2006, 172:156-165.

Pelsers and Glatz, "Detection of brain injury by fatty acid-binding proteins," *Clin. Chem. Lab. Med.*, 2005, 43(8):802-809.

Pinto-Plata et al., "Profiling serum biomarkers in patients with COPD: associations with clinical parameters," *Thorax*, 2007, 62:595-601.

Politi et al., "Elevated plasma N-terminal ProBNP levels in unmedicated patients with major depressive disorder," *Neurosci. Lett.*, 2007, 417:322-325.

Reichek et al., "Antibody responses to bacterial antigens during exacerbations of chronic bronchitis," *Am. Rev. Respir. Dis.*, 1970, 101:238-244.

Rothermundt et al., "Inflammatory markers in major depression and melancholia," *J. Affect. Disord.*, 2001, 63:93-102.

Seemungal et al., "Effect of Exacerbation on Quality of Life in Patients with Chronic Obstructive Pulmonary Disease," *Am. J. Respir. Crit. Care Med.*, 1998, 157:1418-1425.

Sekiyama et al., "A Stress-Induced, Superoxide-Mediated Caspase-1 Activation Pathway Causes Plasma IL-18 Upregulation," *Immunity*, 2005, 22:669-677.

Sin and Man, "Chronic Obstructive Pulmonary Disease as a Risk Factor for Cardiovascular Morbidity and Mortality," *Proc. Am. Thorac. Soc.*, 2005, 2:8-11.

Smith et al., "*Haemophilus influenzae* and *Haemophilus parainfluenzae* in chronic obstructive pulmonary disease," *Lancet*, 1976, 1:1253-1255.

Tsai, "The possible role of tissue-type plasminogen activator and the plasminogen system in the pathogenesis of major depression," *Med. Hypotheses*, 2006, 66:319-322.

von Känel et al., "Effects of Psychological Stress and Psychiatric Disorders on Blood Coagulation and Fibrinolysis: A Biobehavioral Pathway to Coronary Artery Disease?" *Psychosom. Med.*, 2001, 63:531-544.

Wilkinson et al., "Respiratory Syncytial Virus, Airway Inflammation, and $FEV_1$ Decline in Patients with Chronic Obstructive Pulmonary Disease," *Am. J. Respir. Crit. Care Med.*, 2006, 173:871-876.

Yang et al., "Stress-related modulation of matrix metalloproteinase expression," *J. Neuroimmunol.*, 2002, 133:144-150.

Zimmermann-Ivol et al., "Fatty Acid Binding Protein as a Serum Marker for the Early Diagnosis of Stroke," *Mol. Cell. Proteomics*, 2004, 3:66-72.

Carpenter and Bunney, "Adrenal cortical activity in depressive illness," *Am. J. Psychiatry*, 1971, 128:31-40.

Carroll, "Pituitary-adrenal function in depression," *Lancet*, 1968, 1:1373-1374.

Kinder et. al., "Depression and the metabolic syndrome in young adults: findings from the third national health and nutrition examination survey," *Psychosomatic Medicine*, 2004, 66: 316-322.

Park et al., "Vagus nerve stimulation for depression: rationale, anatomical and physiological basis of efficacy and future prospects," *Acta Neurochirurgica Supplementum*, 2007, 97:407-416.

Paus and Barrett, "Transcranial magnetic stimulation (TMS) of the human frontal cortex: implications for repetitive TMS treatment of depression," *Journal of Psychiatry and Neuroscience*, 2004, 29(4):268-279.

Plotsky et al., "Psychoneuroendocrinology of depression. Hypothalamic-pituitary-adrenal axis," *Phychiatr. Clin. North Am.*, 1998, 21(2): 293-307.

Soler-Cataluna et al., "Severe acute exacerbations and mortality in patients with chronic obstructive pulmonary disease," *Thorax*, 2005, 60: 925-931.

Taylor, M. & Fink, M., *Melancholia: The Diagnosis, Pathophysiology, and Treatment of Depressive Illness*, pp. 91-92, Cambridge University Press (2006).

Berthold-Losleben et al., "The TNF-alpha system: functional aspects in depression, narcolepsy and phychopharmacology," *Curr. Neuropharmacol.*, 2002, 3:193-202.

Hung et al., "Insulin sensitivity, proinflammatory markers and adiponectin in young males with different subtypes of depressive disorder," *Clin. Endocrinol.*, 2007, 67(5): 784-789.

Lopez-Leon et al., "Meta-analyses of genetic studies on major depressive disorder," *Mol. Psychiatry*, 2008, 13(8): 772-785.

Pariante et al., "The HPA axis in major depression: classical theories and new developments," *Trends Neurosci.*, 2008, 31(9): 464-468.

Schroeter et al., "Serum markers support disease-specific glial pathology in major depression," *J. Affect. Disord.*, 2008, 3(2-3): 271-280.

* cited by examiner

QUANTITATIVE DIAGNOSTIC METHODS USING MULTIPLE PARAMETERS

CROSS-REFERENCE TO RELATED APPLICATIONS

This application claims benefit of U.S. Provisional Application No. 60/824,471, filed on Sep. 5, 2006, and U.S. Provisional Application No. 60/910,217, filed on Apr. 5, 2007, both of which are incorporated herein by reference in their entirety.

TECHNICAL FIELD

This document relates to materials and methods for diagnosing or assessing a clinical condition in a subject, or determining a subject's predisposition to develop a clinical condition, using algorithms to determine a disease score based a combination of weighted parameters.

BACKGROUND

Most clinical disorders do not arise due to a single biological change, but rather are the result of an interaction of multiple factors. Thus, different individuals affected by the same clinical condition may present with a different range of symptoms or a different extent of symptoms, depending on the specific changes within each individual. The ability to determine disease status on an individual basis thus would be useful for accurate assessment of a subject's specific status. There is a need, however, for reliable methods for diagnosing or determining predisposition to clinical conditions, or for assessing a subject's disease status or response to treatment.

SUMMARY

This document is based in part on the identification of methods for establishing diagnosis, prognosis, or predisposition to particular clinical conditions. The methods can include developing an algorithm that includes multiple parameters such as biomarkers, measuring the multiple parameters, and using the algorithm to determine a quantitative diagnostic score. In some embodiments, algorithms for application of multiple biomarkers from biological samples such as serum or plasma can be developed for patient stratification and identification of pharmacodynamic markers.

The approach described herein can differ from some of the more traditional approaches to biomarkers in the construction of an algorithm versus analyzing single markers or groups of single markers. Algorithms can be used to derive a single value that reflects disease status, prognosis, or response to treatment. As described herein, highly multiplexed microarray-based immunological tools can be used to simultaneously measure of multiple parameters. An advantage of using such tools is that all results can be derived from the same sample and run under the same conditions at the same time. High-level pattern recognition approaches can be applied, and a number of tools are available, including clustering approaches such as hierarchical clustering, self-organizing maps, and supervised classification algorithms (e.g., support vector machines, k-nearest neighbors, and neural networks). The latter group of analytical approaches is likely to be of substantial clinical use.

In one aspect, this document features a process for diagnosing depression in a subject, comprising (a) providing numerical values for a plurality of parameters predetermined to be relevant to depression; (b) individually weighting each of the numerical values by a predetermined function, each function being specific to each parameter; (c) determining the sum of the weighted values; (d) determining the difference between the sum and a control value; and (e) if the difference is greater than a predetermined threshold, classifying the individual as having depression, or, if the difference is not different than the predetermined threshold, classifying the individual as not having depression. The depression can be associated with major depressive disorder.

The parameters can be selected from the group consisting of brain-derived neurotrophic factor (BDNF), interleukin-(IL-)7, IL-10, IL-13, IL-15, IL-18, fatty acid binding protein (FABP), alpha-1 antitrypsin (A1AT), beta-2 macroglobulin (B2M), factor VII, epithelial growth factor (EGF), alpha-2-macroglobulin (A2M), glutathione S-transferase (GST), RANTES, tissue inhibitor of matrix metalloproteinase-1 (TIMP-1), plasminogen activator inhibitor-1 (PAI-1), thyroxine, and cortisol. The parameters can be selected from the group consisting of BDNF, A2M, IL-10, IL-13, IL-18, cortisol, and thyroxine (e.g., BDNF, A2M, IL-10, and IL-13; BDNF, A2M, IL-10, and IL-18; BDNF, A2M, IL-13, and IL-18; BDNF, A2M, and IL-10; BDNF, A2M, and IL-13; or BDNF, A2M, and IL-18). The numerical values can be biomarker levels in a biological sample from the subject. The biological sample can be whole blood, serum, plasma, urine, or cerebrospinal fluid. The subject can be a human. The predetermined threshold can be statistical significance (e.g., $p<0.05$). Methods for determining statistical significance can include those routinely used in the art, for example.

In another aspect, this document features a process for diagnosing depression in a subject, comprising (a) providing numerical values for a plurality of parameters predetermined to be relevant to depression, individually weighting each of the numerical values by a predetermined function, each function being specific to each parameter, determining the sum of the weighted values, determining the difference between the sum and a control value; and (b) if the difference is greater than a predetermined threshold, classifying the individual as having depression, or, if the difference is not greater than the predetermined threshold, classifying the individual as not having depression.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
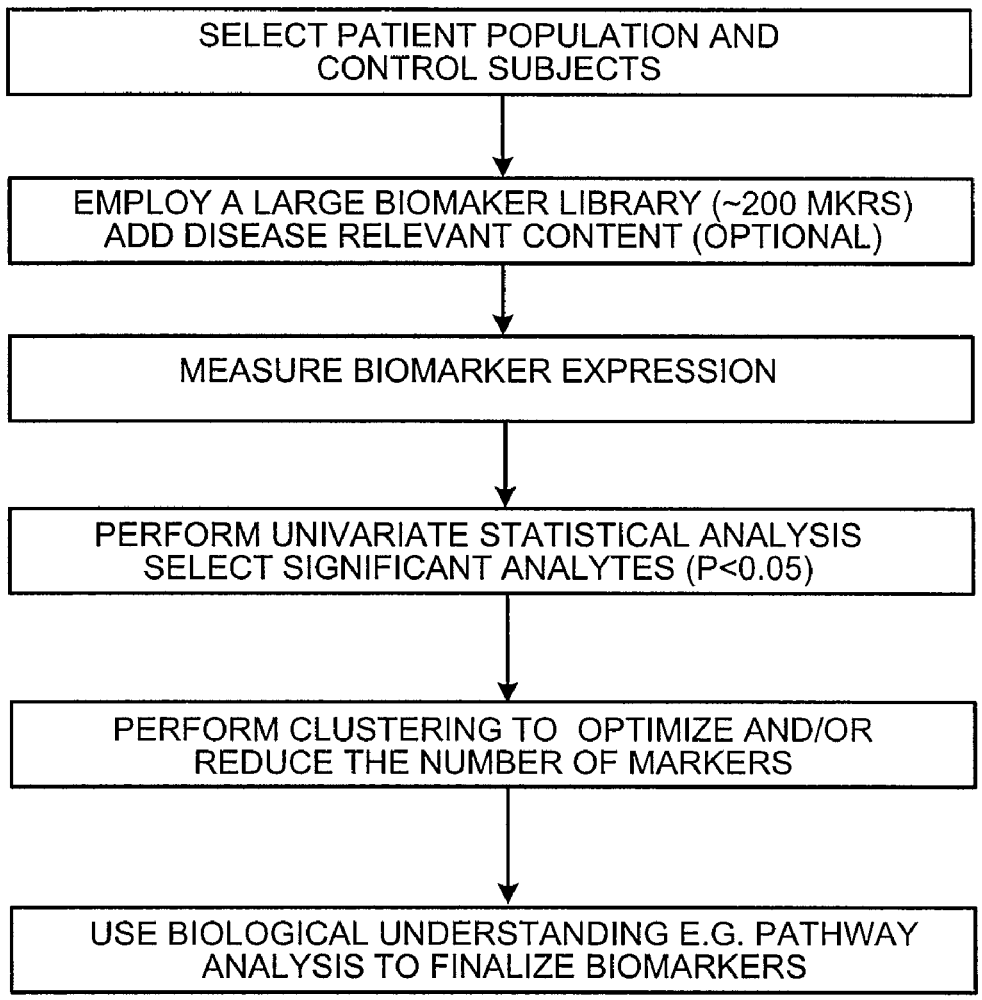
FIG. 1 is a flow diagram outlining the selection of biomarkers.

This document is based in part on the identification of methods for establishing a diagnosis, prognosis, or predisposition to particular clinical conditions by developing an algorithm, evaluating (e.g., measuring) multiple parameters, and using the algorithm to determine a quantitative diagnostic score. Algorithms for application of multiple biomarkers from biological samples such as serum or plasma can be developed for patient stratification and identification of pharmacodynamic markers. The approach described herein differs from some of the more traditional approaches to biomarkers in the construction of an algorithm versus analyzing single markers or groups of single markers.

Algorithms

Algorithms for determining diagnosis, prognosis, status, or response to treatment, for example, can be determined for any clinical condition. The algorithms used in the methods provided herein can be mathematic functions containing multiple parameters that can be quantified using, for example, medical devices, clinical evaluation scores, or biological/chemical/physical tests of biological samples. Each mathematic function can be a weight-adjusted expression of the levels of parameters determined to be relevant to a selected clinical condition. The algorithms generally can be expressed in the format of Formula 1:

$$\text{Diagnostic score} = f(x1, x2, x3, x4, x5 \ldots xn) \quad (1)$$

The diagnostic score is a value that is the diagnostic or prognostic result, "f" is any mathematical function, "n" is any integer (e.g., an integer from 1 to 10,000), and x1, x2, x3, x4, x5 . . . xn are the "n" parameters that are, for example, measurements determined by medical devices, clinical evaluation scores, and/or tests results for biological samples (e.g., human biological samples such as blood, urine, or cerebrospinal fluid).

The parameters of an algorithm can be individually weighted. An example of such an algorithm is expressed in Formula 2:

$$\text{Diagnostic score} = a1*x1 + a2*x2 - a3*x3 + a4*x4 - a5*x5 \quad (2)$$

Here, x1, x2, x3, x4, and x5 can be measurements determined by medical devices, clinical evaluation scores, and/or test results for biological samples (e.g., human biological samples), and a1, a2, a3, a4, and a5 are weight-adjusted factors for x1, x2, x3, x4, and x5, respectively.

The diagnostic score can be used to quantitatively define a medical condition or disease, or the effect of a medical treatment. For example, an algorithm can be used to determine a diagnostic score for a disorder such as depression. In such an embodiment, the degree of depression can be defined based on Formula 1, with the following general formula:

$$\text{Depression diagnosis score} = f(x1, x2, x3, x4, x5 \ldots xn)$$

The depression diagnosis score is a quantitative number that can be used to measure the status or severity of depression in an individual, "f" is any mathematical function, "n" can be any integer (e.g., an integer from 1 to 10,000), and x1, x2, x3, x4, x5 . . . xn are, for example, the "n" parameters that are measurements determined using medical devices, clinical evaluation scores, and/or test results for biological samples (e.g., human biological samples).

To determine what parameters are useful for inclusion in a diagnostic algorithm, a biomarker library of analytes can be developed, and individual analytes from the library can be evaluated for inclusion in an algorithm for a particular clinical condition. In the initial phases of biomarker library development, the focus may be on broadly relevant clinical content, such as analytes indicative of inflammation, Th1 and Th2 immune responses, adhesion factors, and proteins involved in tissue remodeling (e.g., matrix metalloproteinases (MMPs) and tissue inhibitors of matrix metalloproteinases (TIMPs)). In some embodiments (e.g., during initial library development), a library can include a dozen or more markers, a hundred markers, or several hundred markers. For example, a biomarker library can include a few hundred protein analytes. As a biomarker library is built, new markers can be added (e.g., markers specific to individual disease states, and/or markers that are more generalized, such as growth factors). In some embodiments, analytes can be added to expand the library and to increase specificity beyond the inflammation, oncology, and neuropsychological foci by addition of disease related proteins obtained from discovery research (e.g., using differential display techniques, such as isotope coded affinity tags (ICAT) or mass spectroscopy).

The addition of a new analyte to a biomarker library can require a purified or recombinant molecule, as well as the appropriate antibody to capture and detect the new analyte. It is noted that while application of a biomarker library to conventional ELISA platforms can require multiple antibodies for each analyte, use of the Precision Human Biolaboratories, Inc. (PHB, Durham, N.C.) Molecular Interaction Measurement System (MIMS) as described herein requires a single specific antibody for each analyte. Although discovery of individual "new or novel" biomarkers is not necessary for developing useful algorithms, such markers can be included. The MIMS platform and other technologies that are suitable for multiple analyte detection methods as described herein typically are flexible and open to addition of new analytes.

This document provides multiplexed detection systems that can provide robust and reliable measurement of analytes relevant to diagnosing, treating, and monitoring clinical conditions. The biomarker panels can be expanded and transferred to label-free arrays, and algorithms can be developed to support clinicians and clinical research.

Custom antibody array(s) can be designed, developed, and analytically validated for about 25-50 antigens. Initially, a panel of about 5 to 10 (e.g., 5, 6, 7, 8, 9, or 10) analytes can be chosen based on their ability to, for example, distinguish affected from unaffected subjects, or to distinguish between stages of disease in patients from a defined sample set. An enriched database, however, usually one in which more than 10 significant analytes are measured, can increase the sensitivity and specificity of test algorithms.

It is noted that such approaches also can be applied to other biological molecules including, without limitation, DNA and RNA.

Selection of Individual Parameters

In the construction of libraries or panels, the markers and parameters can be selected by any of a variety of methods. The primary driver for construction of a disease specific library or panel can be knowledge of a parameter's relevance to the disease. To construct a library for diabetes, for example, understanding of the disease would likely warrant the inclusion of blood glucose levels. Literature searches or experimentation also can be used to identify other parameters/markers for inclusion. In the case of diabetes, for example, a literature search might indicate the potential usefulness of hemoglobin A1c (HbAC), while specific knowledge or experimentation might lead to inclusion of the inflammatory markers tumor necrosis factor (TNF)-α receptor 2, interleukin (IL)-6, and C-reactive protein (CRP), which have been shown to be elevated in subjects with type II diabetes.

FIG. 1 is a flow diagram detailing the first steps that can be included in development of a disease specific library or panel for use in determining, e.g., diagnosis or prognosis. The process can include two statistical approaches: 1) testing the distribution of biomarkers for association with the disease by univariate analysis; and 2) clustering the biomarkers into groups using a tool that divides the biomarkers into non-overlapping, uni-dimensional clusters, a process similar to principal component analysis. After the initial analysis, a subset of two or more biomarkers from each of the clusters can be identified to design a panel for further analyses. The selection typically is based on the statistical strength of the markers and current biological understanding of the disease.

Figure 2:
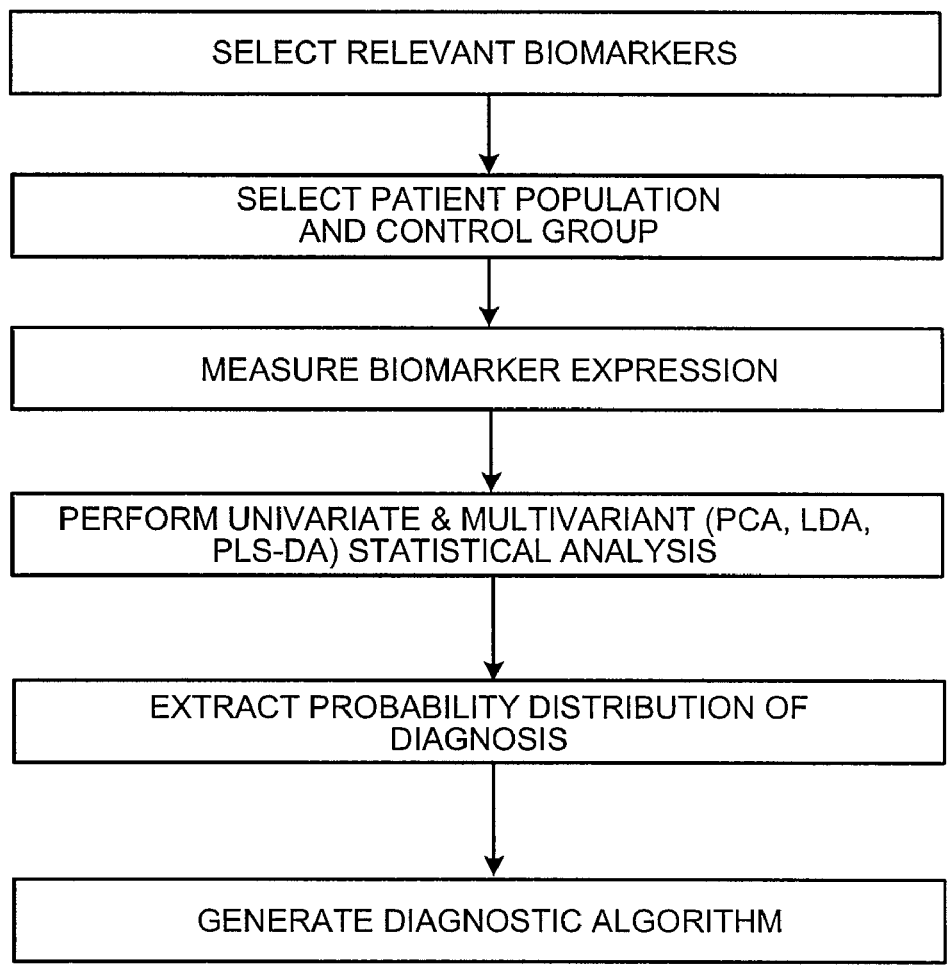
FIG. 2 is a flow diagram for the development of a disease specific library or panel with an algorithm for diagnostic development.

FIG. 2 is a flow diagram depicting steps that can be included to develop a disease specific library or panel for use in establishing diagnosis or prognosis, for example. As shown in FIG. 2, the selection of relevant biomarkers need not be dependant upon the selection process described in FIG. 1, although the first process is efficient and can provide an experimentally and statistically based selection of markers. The process can be initiated, however, by a group of biomarkers selected entirely on the basis of hypothesis and currently available data. The selection of a relevant patient population and appropriately matched (e.g., for age, sex, race, BMI, etc.) population of normal subjects typically is involved in the process. In some embodiments, patient diagnoses can be made using state of the art methodology and, in some cases, by a single group of physicians with relevant experience with the patient population. Biomarker expression levels can be measured using the MIMS instrument or any other suitable technology, including single assays (e.g., ELISA or PCR). Univariate and multivariate analyses can be performed using conventional statistical tools (e.g., T-tests, principal components analysis (PCA), linear discriminant analysis (LDA), or Binary Logistic Regression).

Figure 3:
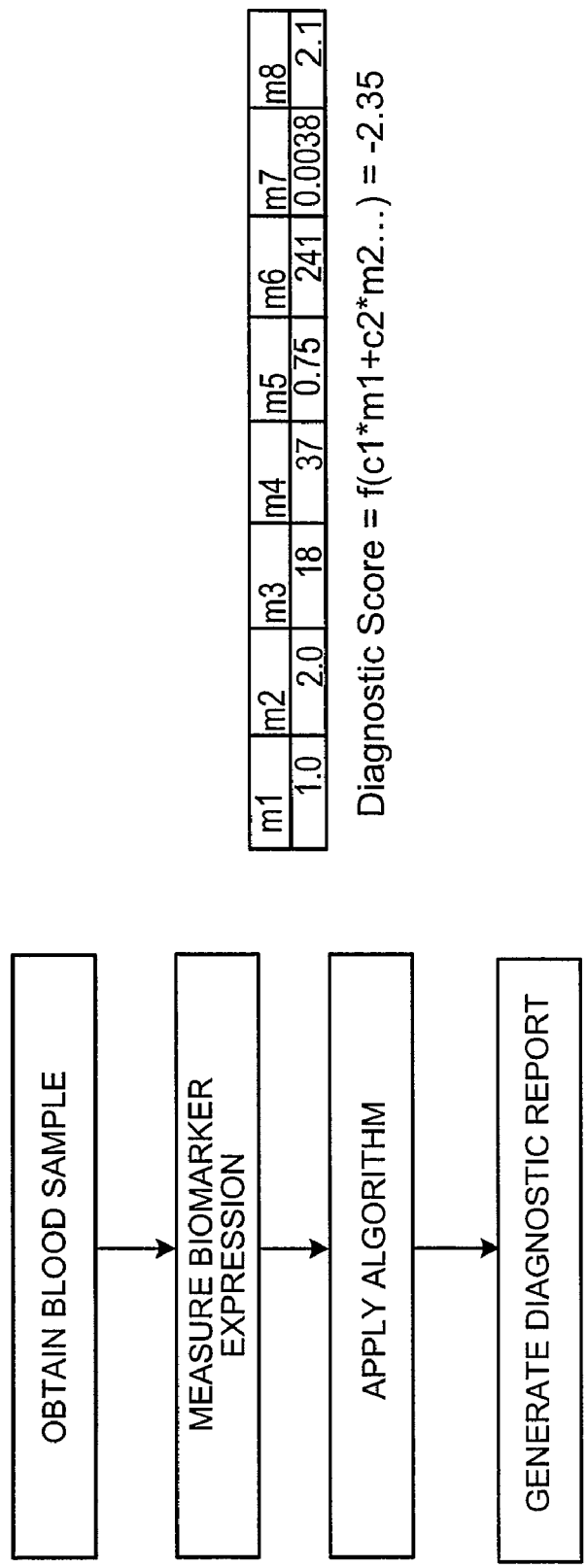
FIG. 3 is a flow diagram for development of a diagnostic score.

FIG. 3 is a flow diagram depicting steps that can be included in establishing a score for diagnostic development and application. The process can involve obtaining a biological sample (e.g., a blood sample) from a subject to be tested. Depending upon the type of analysis being performed, serum, plasma, or blood cells can be isolated by standard techniques. If the biological sample is to be tested immediately, the sample can be maintained at room temperature; otherwise the sample can be refrigerated or frozen (e.g., at −80° C.) prior to assay. Biomarker expression levels can be measured using a MIMS instrument or any other suitable technology, including single assays such as ELISA or PCR, for example. Data for each marker are collected, and an algorithm is applied to generate a diagnostic score. The diagnostic score, as well as the individual analyte levels, can be provided to a clinician for use in establishing a diagnosis for the subject.

Analyte Measurement

Any suitable method(s) can be used to quantify the parameters included in a diagnostic/prognostic algorithm. For example, analyte measurements can be obtained using one or more medical devices or clinical evaluation scores to assess a subject's condition, or using tests of biological samples to determine the levels of particular analytes. As used herein, a "biological sample" is a sample that contains cells or cellular material, from which nucleic acids, polypeptides, or other analytes can be obtained. Useful biological samples include, without limitation, urine, blood, serum, plasma, cerebrospinal fluid, pleural fluid, bronchial lavages, sputum, peritoneal fluid, bladder washings, secretions (e.g., breast secretions), oral washings, swabs (e.g., oral swabs), tissue samples, touch preps, and fine-needle aspirates.

Measurements can be obtained separately for individual parameters, or can be obtained simultaneously for a plurality of parameters. Any suitable platform can be used to obtain measurements for parameters. Useful platforms for simultaneously quantifying multiple parameters include, for example, those described in U.S. Provisional Application Nos. 60/910,217 and 60/824,471, as well as PCT Publication No. WO2007/067819, all of which are incorporated herein by reference in their entirety.

An example of a useful platform utilizes MIMS label-free assay technology, which has been developed by PHB. Briefly, local interference at the boundary of a thin film can be the basis for optical detection technologies. For biomolecular interaction analysis, glass chips with an interference layer of $SiO_2$ can be used as a sensor. Molecules binding at the surface of this layer increase the optical thickness of the interference film, which can be determined as set forth in U.S. Provisional Application Nos. 60/910,217 and 60/824,471, for example.

Figure 4:
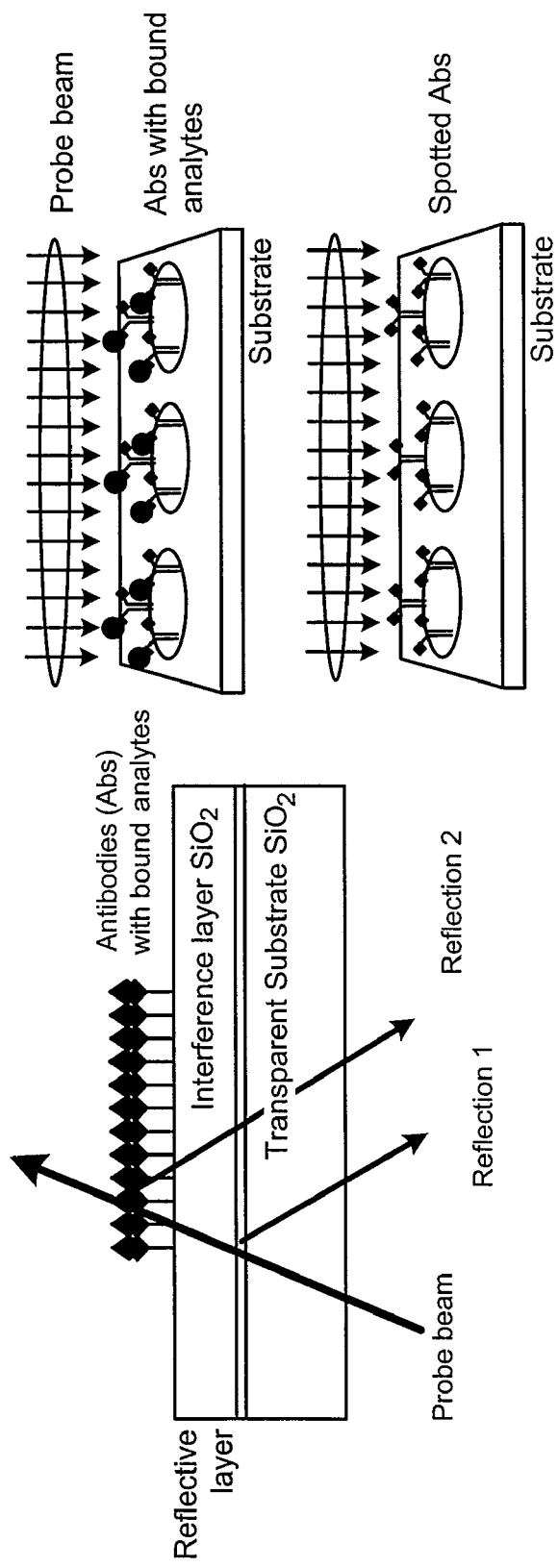
FIG. 4 is a pair of illustrations depicting the binding of an antigen to its specific antibody on a substrate, resulting in an increase in the optical thickness of the interference film when a light beam is directed at the substrate (left panel). The right panel depicts a substrate having three discrete spots of antibodies, with analytes bound specifically thereto (top panel).

FIG. 4 illustrates the binding of an antigen to its specific antibody on an exemplary biochip described in the above referenced patent documents. This binding results in an increase in the optical thickness of the interference film. As illustrated, this biochip includes having a transparent substrate and a transparent thin-film layer as an interference layer. An optional reflective thin-film layer is deposited between the substrate and the transparent thin-film layer in implementations when the refractive index of the substrate is similar to the transparent thin-film layer. The biochip is illuminated by a probe beam of light. A first reflected light beam is reflected at the interface between the substrate and the transparent thin-film layer or the middle reflective thin-film layer. The input probe beam is also reflected as a second reflected light beam off the top surface of the transparent thin-film layer. The two reflected beams are analyzed to obtain height information of the substrate and the transparent thin-film layer before immobilizing reagents on the reagent immobilizing sites.

The biochip in FIG. 4 can be designed to include multiple reagent immobilizing sample sites arranged in an array on the surface of the transparent thin-film layer for immobilizing reagent molecules. The substrate can be designed to include one or more calibration structures deposited on the top surface to provide on-chip calibration. In addition, a set of alignment marks can be formed on the substrate to enable a scanner or imager to identify and locate a target spot (e.g., a reagent immobilizing sample site). These alignment marks can be implemented to encode location information such as the position coordinates (x,y) of the target spots. An position encoding scheme can include a bar code, or a simple number. In some implementations, the alignment markers can include markers with high image contrast for easy detection. The alignment markers can so be used as alignment visual markers to guide a x-y moving stage holding a biochip to setup and configure an initial scanning position. Such alignment markers can enhance accuracy of aligning different scan data together. Details of these and other features are described in U.S. Provisional Application Nos. 60/910,217 and 60/824, 471 and PCT Publication No. WO2007/067819.

To measure molecular interactions, an array of different antibodies can be immobilized on a sensor chip surface, and a hyperspectrum imaging system can be used to scan the chip to acquire interference-related spectrum information over the entire sensor chip surface. In one implementation, this hyperspectrum imaging system for detecting molecular interaction includes a light probe having a light source designed to direct a probe beam of light along an optical light path, one or more optical lenses located along the light path, and an optical grating located along the light path. The optical grating is designed to switch between a zero optical mode to turn off the dispersive function of the grating and a first optical mode to diffract input light into the first diffraction order of the grating. The optical probe includes an optical slit designed to switch between a position on the light path and a position off the light path. A sample stage is also included with the imaging system with the sample stage designed to hold and move a biochip along a predetermined plane perpendicular to the light path. The imaging system further includes an image sensor located along the light path with the image sensor designed to capture the probe beam of light reflected off the substrate. Implementations can optionally include one or more of the following features. The imaging system can include an imaging mode controller designed to switch the optical grating between the zero optical mode and the first optical mode. The imaging mode controller can also move the optical slit between the position on the light path and the position off the light path. In some implementations, the imaging mode controller can also switch the optical grating to the first optical mode and move the optical slit on the light path in such a manner as to direct a single line of the reflected beam of light is through the optical slit and the optical grating to disperse the single line of the reflected beam of light into spectral components.

In addition, implementations can optionally include one or more of the following features. The imaging system can include one or more additional optical slits and optical gratings. Also, the imaging mode controller can be designed to switch the optical gratings to the first optical mode and move the optical slits on the light path in such a manner as to direct a different line of the reflected beam of light through each of the optical slits and the optical gratings to disperse each line of the reflected beam of light into spectral components. image sensor can be designed to determine the height at the reagent immobilizing area based on the spectral components of the reflected beam of light. The light source can be designed to direct a probe beam of light having a coherent length based on a height of the substrate. Further the image sensor can include a charge coupled device (CCD) image sensor. Alternatively, the image sensor can include a complementary metal oxide semiconductor (CMOS) image sensor.

Figure 5:
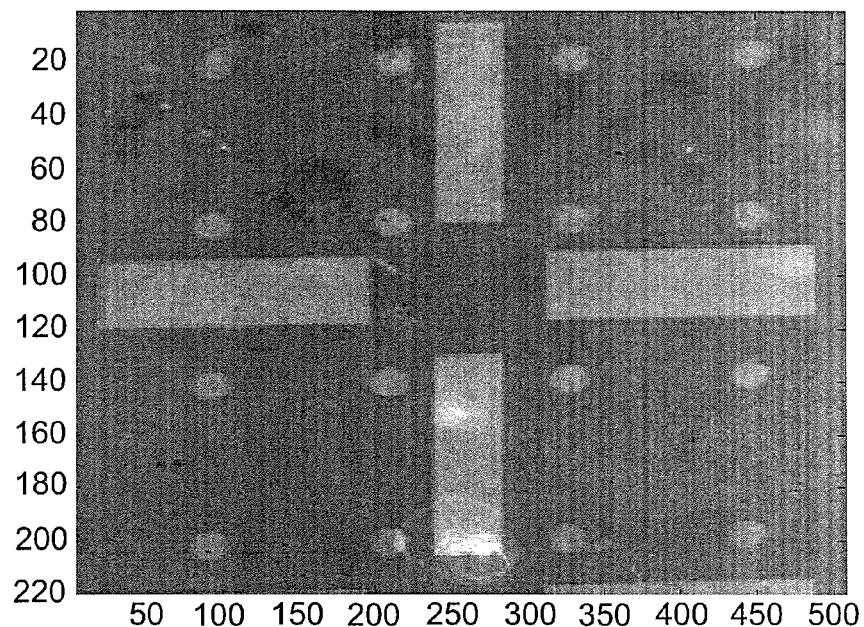
FIG. 5 is a two-dimensional view of anti-interleukin-1 beta (anti-IL-1 beta) printed nanostructured chip (16 spots are shown).
Figure 6:
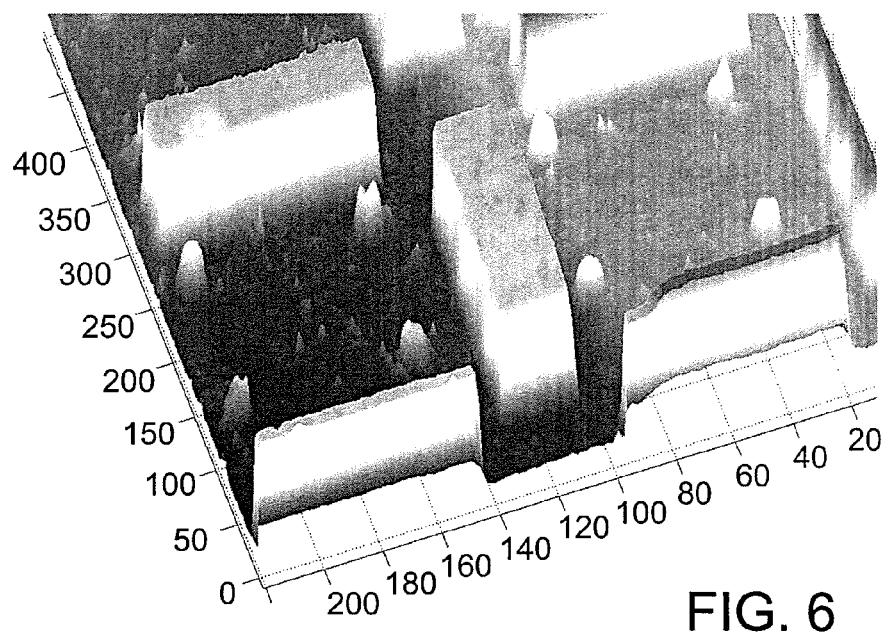
FIG. 6 is a three-dimensional view of the front portion of the same chip shown in FIG. 5.
Figure 7:
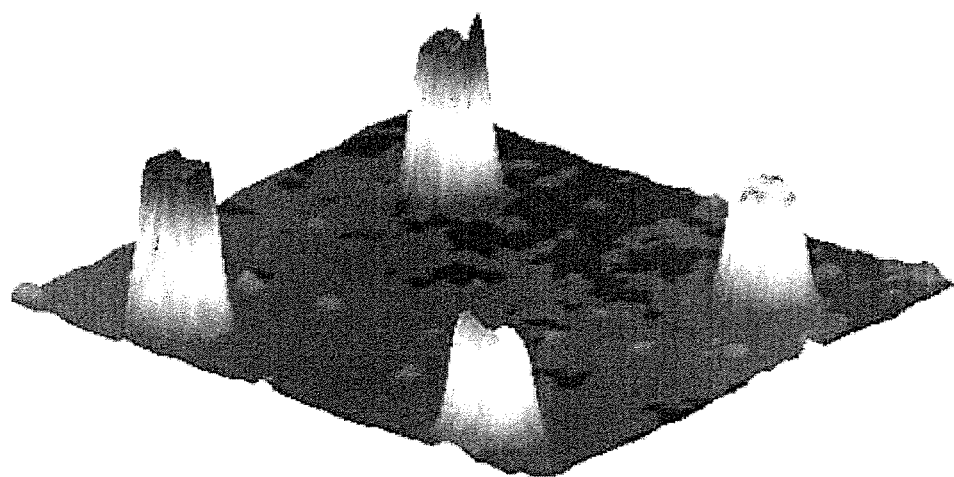
FIG. 7 a three-dimensional view of the IL-1 beta antibody reacted with IL-1 beta standard. The graph in the right panel indicates the changes in peak height before (upper peaks) and after (lower peaks) reaction with IL-1 beta.
Figure 7:
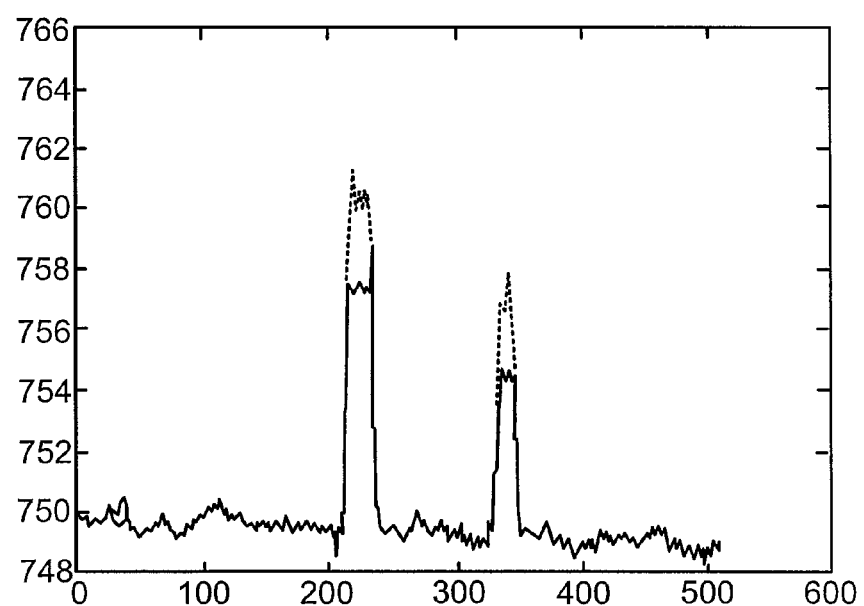

FIGS. 5-7 provide examples of the data output from a MIMS instrument. In particular, FIG. 5 shows a two-dimensional view of anti-IL-1 beta printed (about 0.15 pg) on the nanostructured chip (16 spots are shown). A three-dimensional view of the front portion of the same area is shown in FIG. 6. The nanobars are 20 nanometers high, and the volume of the peak is proportional to the concentration of antibody printed on the surface. FIG. 7 shows a three-dimensional view of the IL-1 beta antibody (2-fold concentrations) reacted with an IL-1 beta standard. The graph in the right panel indicates the changes in peak height before (upper peaks) and after (lower peaks) reaction with IL-1 beta.

Another example of platform useful for multiplexing is the FDA approved, flow-based Luminex assay system (xMAP; World Wide Web at luminexcorp.com). This multiplex technology uses flow cytometry to detect antibody/peptide/oligonucleotide or receptor tagged and labeled microspheres. Since the system is open in architecture, Luminex can be readily adapted to host particular disease panels.

The invention will be further described in the following examples, which do not limit the scope of the invention described in the claims.

EXAMPLES

Example 1

Diagnostic Markers of Depression

Methods provided herein were used to develop an algorithm for determining depression scores that are useful to, for example, diagnose or determine predisposition to major depressive disorder (MDD), or evaluate response to antidepressive therapeutics. The development of psychotropic drugs has relied on the quantification of disease severity through psychopathological parameters (e.g., the Hamilton scale for depression). Subjective factors and lack of a proper definition inevitably influence such parameters. Similarly, diagnostic parameters for enrollment of psychiatric patients in phase II and phase III clinical studies are centered on the assessment of disease severity and specificity by measurement of symptomatological scales, and there are no validated biological correlates for disease trait and state that could help in patient selection. In spite of recent progress in molecular diagnostics, the potential information contained within the patient genotype on the likely phenotypic response to drug treatment has not been effectively captured, particularly in non-research settings.

The immune system has a complex and dynamic relationship with the nervous system, both in health and disease. The immune system surveys the central and peripheral nervous systems, and can be activated in response to foreign proteins, infectious agents, stress and neoplasia. Conversely, the nervous system modulates immune system function both through the neuroendocrine axis and through vagus nerve efferents. When this dynamic relationship is perturbed, neuropsychiatric diseases can result. In fact, several medical illnesses that are characterized by chronic inflammatory responses (e.g., rheumatoid arthritis) have been reported to be accompanied by depression. In addition, administration of proinflammatory cytokines (e.g., in cancer or hepatitis C therapies) can induce depressive symptomatology. Administration of proinflammatory cytokines in animals induces "sickness behavior," which is a pattern of behavioral alterations that is very similar to the behavioral symptoms of depression in humans. Thus, the "Inflammatory Response System (IRS) model of depression" (Maes (1999) *Adv. Exp. Med. Biol.* 461:25-46) proposes that proinflammatory cytokines, acting as neuromodulators, represent key factors in mediation of the behavioral, neuroendocrine and neurochemical features of depressive disorders.

Multiplexed detection systems such as those described herein were used to phenotype molecular correlates of depression. Preliminary studies indicated the value in using multiplexed antibody arrays to develop a panel of biomarkers in populations with MDD. The availability of biological markers reflecting psychiatric state (e.g., the type of pathology, severity, likelihood of positive response to treatment, and vulnerability to relapse) will greatly impact both the appropriate diagnosis and treatment of depression.

The systematic, highly parallel, combinatorial approach to assemble "disease specific signatures" using algorithms as described herein is used to determine the status of or predisposition to MDD, and also is used to predict an individual's response to therapy. Toward that end, a biomarker library—a collection of tests useful to quantify proteins expressed in human serum—was developed.

Results

Panels were initially developed by analyzing results using two statistical approaches: 1) testing the distribution of biomarkers for an association with disease by univariate analysis; and 2) clustering the biomarkers into groups using a variable clustering (VARCLUS) tool that divides the biomarkers into non-overlapping uni-dimensional clusters, a process similar to principal component analysis. Each cluster's predictive value was determined by computing individual cluster centroid's partial regression coefficient with the affected group, using partial least squares discriminant analysis (PLS-DA). After the initial analysis, the panel was made functionally redundant, and a subset of 2-4 biomarkers from each of the 8 clusters with the highest statistical significance was identified. The final selection was based on the statistical strength of the markers and current biological understanding of the disease.

Preliminary studies included patients meeting the criteria for recurrent major depressive disorder according to the DSM IV scale. The studies of depression described herein were conducted on a population of Ashkenazi Jewish (AJ) males, which was chosen for the studies due to the relative genetic homogeneity of the population and to limit gender-related differences. In addition, the frequency of several genes responsible for "single-gene" disorders and disease predisposition is higher among Ashkenazi Jews than among Sephardic Jews and non-Jews. All patients studied were from a single medical center to avoid site-related differences in the diagnosis of depression. To provide a sufficient number of subjects (110 total, including 55 controls and 55 depressed individuals), males between the ages of 18 and 70 years were included.

Figure 8:
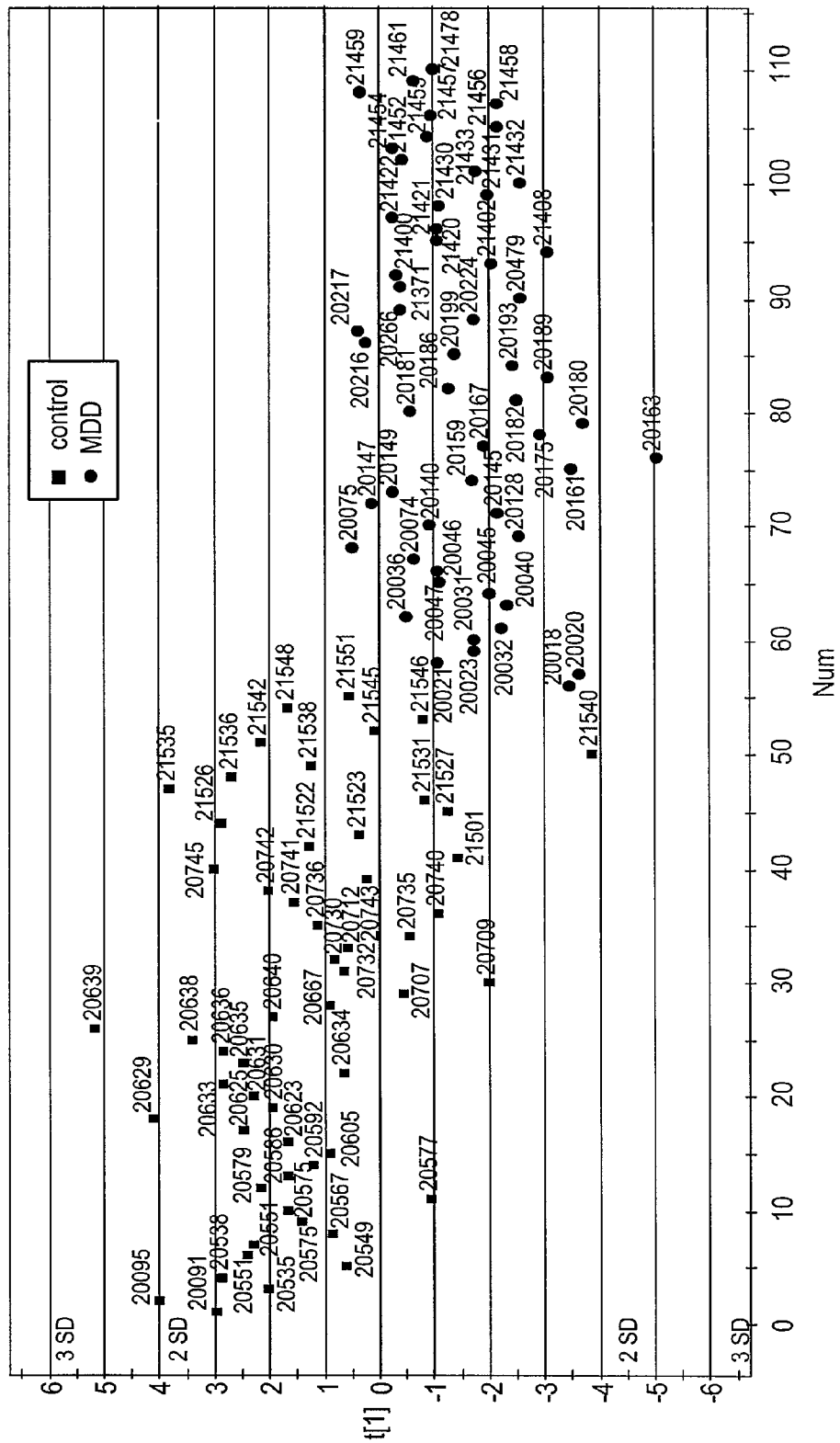
FIG. 8 is a graph plotting diagnostic depression scores generated using a multivariate analysis of sera from control (squares) and major depressive disorder (MDD) (circles) individuals, which were analyzed using a biomarker library panel of about 85 serum protein analytes.

Multivariate analysis using the Partial Least Squares based software SIMCA-P (Umetrics, Umea, Sweden) readily segregated the 55 controls from the 55 depressed members of the AJ male cohort. FIG. 8 shows the results of multivariate analysis of sera from control and MDD patients, which were analyzed using a biomarker library panel of about 85 serum protein analytes. Similar results were obtained for a subset of subjects ranging from 30 to 49 years of age. The library of 85 analytes that was used for the initial study was biased toward inflammatory markers. The library also included chemokines, enzymes involved in tissue remodeling (e.g., MMPs and TIMPs), and several hormones (e.g., human growth hormone and erythropoietin, which had been shown to be elevated in the CSF of depressed patients).

Two statistical approaches were then used for biomarker assessment and algorithm development: (1) univariate analysis for testing the distribution of biomarkers for association with MDD; and (2) linear discriminant analysis (LDA) and binary logistic regression for algorithm construction.

Univariate analysis of individual analyte levels: Using the Students T test, serum levels of each of the analytes tested using Luminex multiplex technology were analyzed for comparison of depressed versus normal subjects. The level of significance was set at $\alpha \leq 0.05$. The results of this analysis for sixteen significant analytes are shown in Table 1. Results of the analysis for a different combination of seven biomarkers is shown in Table 2. The potential relationship of each analyte to depression is indicated in Table 3.

TABLE 1

Mean serum levels and p values for 16 MDD biomarkers

| Analyte | Mean Serum Level MDD | Mean Serum Level Control | p value |
| --- | --- | --- | --- |
| IL-13 | 17.42 pg/ml | 40.35 pg/ml | 1.20E−06 |
| IL-7 | 10.52 pg/ml | 22.92 pg/ml | 2.80E−05 |
| GST | 8.13 ng/ml | 25.62 ng/ml | 0.0005 |
| IL-18 | 333.7 pg/ml | 267 pg/ml | 0.0018 |
| A2M | 0.996 mg/ml | 0.776 mg/ml | 0.0011 |
| IL-15 | 0.955 pg/ml | 1.51 pg/ml | 0.0005 |
| IL-10 | 3.4 pg/ml | 5.55 pg/ml | 0.0007 |
| Factor VII | 373.4 ng/ml | 455.1 ng/ml | 0.0007 |
| EGF | 56.08 pg/ml | 90.30 pg/ml | 0.01 |
| FABP | 2.15 ng/ml | 1.57 ng/ml | 0.004 |
| PAI-1 | 76.58 pg/ml | 89.66 pg/ml | 0.01 |
| BDNF | 20.12 ng/ml | 17.36 ng/ml | 0.012 |
| RANTES | 41.36 pg/ml | 34.49 pg/ml | 0.0049 |
| TIMP-1 | 173.3 ng/ml | 194.2 ng/ml | 0.038 |
| Alpha 1 Antitrypsin | 1.77 mg/ml | 1.65 mg/ml | 0.0085 |
| Beta 2 Microglobulin | 1.87 mg/ml | 2.17 mg/ml | 0.0125 |

TABLE 2

Mean serum levels and p values for 7 MDD Biomarkers

| Analyte | Serum Level Normal Mean | Serum Level MDD Mean | p value |
| --- | --- | --- | --- |
| IL-10 | 5.84 pg/ml | 2.304 pg/ml | 0.008 |
| IL-13 | 48 pg/ml | 13.73 pg/ml | 0.0002 |
| IL-18 | 268 pg/ml | 424.2 pg/ml | 0.0038 |
| Cortisol | 269 ng/ml | 390 ng/ml | 0.0028 |
| A2M | 0.959 mg/ml | 1.313 mg/ml | 0.009 |
| Thyroxine | 6.23 ng/ml | 5.35 ng/ml | 0.016 |
| BDNF | 23.09 ng/ml | 17.76 ng/ml | 0.029 |

TABLE 3

| Analyte | Relationship to Depression |
| --- | --- |
| IL-13 | IL-13 usually acts as an anti-inflammatory cytokine |
| IL-7 | IL-7 may be a neuronal growth factor |
| GST | stress related; tricyclics reduce level |
| IL-18 | stress related release of IL-18 in CNS and plasma |
| A2M | acute phase protein associated with inflammatory disease |
| IL-15 | IL-15 is a novel proinflammatory cytokine |
| IL-10 | IL-10 usually acts as an anti-inflammatory cytokine |
| Factor VII | one of the central proteins in the coagulation cascade. |
| EGF | growth factor involved in neuroplasticity & the EGF-R TK cascade |
| FABP | FABPs control intracellular transport and storage of lipids |
| PAI-1 | tPA/plasminogen system may play a role in MDD pathogenesis |
| BDNF | neuroplasticity, lower in MDD, responds to treatment |
| RANTES | RANTES may serve to amplify inflammatory responses in CNS |
| TIMP-1 | extracellular matrix remodeling in physiological & pathological processes |
| A1AT | reduced activity of peptidases can occur in MDD |
| B2M | can be associated with chronic inflammatory conditions |
| Cortisol | stress hormone that can be elevated in MDD |
| Thyroxine ($T_4$) | serum $T_4$ is important for the action of thyroid hormones in the brain |

Figure 9:
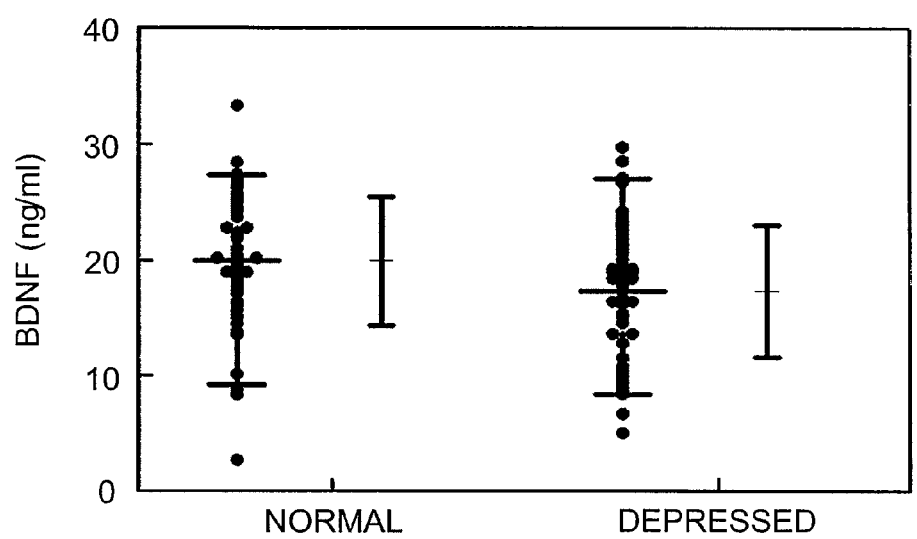
FIG. 9 is a graph plotting brain-derived neurotrophic factor (BDNF) levels in the serum of normal male subjects and male MDD patients. The dots represent measurements for each subject, with the embedded median and the 5 and 95 percentile whiskers. The adjacent lines indicate the means and the standard deviations from the mean.
Figure 10:
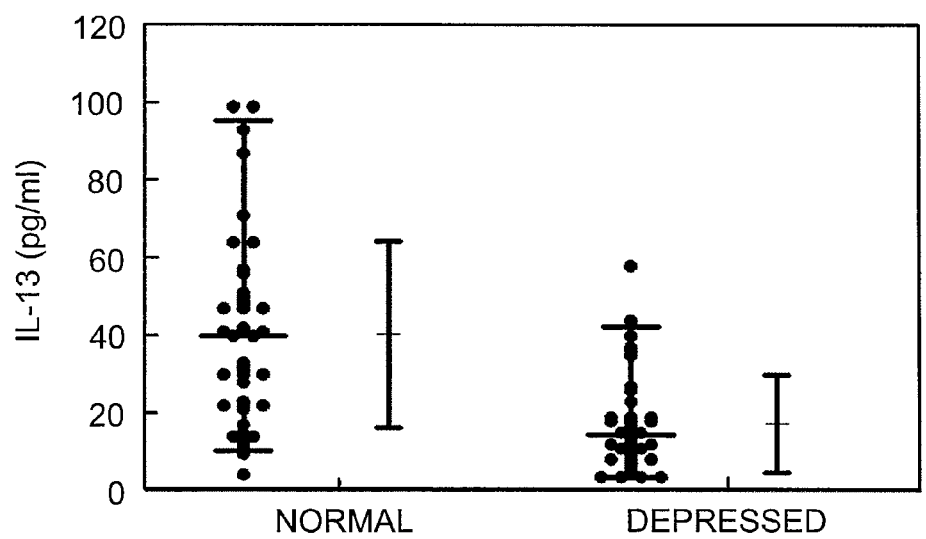
FIG. 10 is a graph plotting serum interleukin (IL)-13 levels in normal male subjects and male MDD patients. The dots represent measurements for each subject, with the embedded median and the 5 and 95 percentile whiskers. The adjacent lines indicate the means and the standard deviations from the mean.

As examples of the data presented in Tables 1 and 2, FIGS. 9 and 10 show the serum levels of BDNF and IL-13, respectively, in MDD patients and in normal subjects. The mean level of BDNF in the MDD group (17.76±5.27) was lower than in the normal subject group (23.06±5.45). While univariate analysis identified BDNF as a marker with statistical significance (p=0.029), the ranges of BDNF levels for the two groups overlap significantly. Thus, serum BDNF by itself is not a good predictor of MDD. Similarly, univariate analysis identified IL-13 as the marker with highest statistical significance (p=0.0002), suggesting that it could be a class predictor. As shown in FIG. 10, however, there was significant overlap in the range of serum IL-13 levels between MDD subjects and controls. In fact, no single analyte exhibited a clear separation with non-overlapping levels for the patient-control subject comparisons. Therefore, single analytes cannot be used as a class predictor for MDD.

PCA and PLS-DA: PCA is mathematically defined as an orthogonal linear transformation that transforms the data to a new coordinate system such that the greatest variance by any projection of the data comes to lie on the first coordinate (called the first principal component), the second greatest variance on the second coordinate, and so on. PCA can be used for dimensionality reduction in a data set by retaining those characteristics of the data set that contribute most to its variance, by keeping lower-order principal components and ignoring higher-order ones. Such low-order components often contain the "most important" aspects of the data.

PLS-DA was performed in order to sharpen the separation between groups of observations, by rotating PCA components such that a maximum separation among classes is obtained, and to understand which variables carry the class separating information. PLS-DA and other techniques were used to demonstrate the segregation of normal subjects and depressed patients using the MDD panel to measure serum levels of 16 analytes, five analytes, four analytes, and three analytes as examples.

An Algorithm Based Upon Linear Discriminant Analysis (LDA): In order to identify the analytes that contribute the most to discrimination between classes (e.g., depressed vs. normal), a stepwise method of LDA from SPSS 11.0 for Windows was used with following settings: Wilks' lambda ($\Lambda$) method was used to select analytes that maximize the cluster separation and analyte entrance into the model was controlled by its F-value. A large F-value indicates that the level of the particular analyte is different between the two groups, and a small F-value (F<1) indicates that there is no difference. In this method, the null hypothesis is rejected for small values of $\Lambda$. Thus, the aim was to minimize $\Lambda$.

To construct a list of analyte predictors, the F-values for each of the analytes was calculated. Starting with the analyte having the largest F-value (the analyte that differs the most between the two groups), the value of $\Lambda$ was determined. The analyte with the next largest F-value was then added to the list and $\Lambda$ was recalculated. If the addition of the second analyte lowered the value of $\Lambda$, it was kept in the list of analyte predictors. The process of adding analytes one at a time was repeated until the reduction of $\Lambda$ no longer occurred.

Cross-validation, a method for testing the robustness of a prediction model, was then carried out. To cross-validate a prediction model, one sample is removed and set aside, the remaining samples are used to build a prediction model based on the pre-selected analyte predictors, and a determination is made as to whether the new model is able to predict the one sample not used in building the new model correctly. This process is repeated for all samples one at a time, and a cumulative cross-validation rate then can be calculated. The final list of analyte predictors was determined by manually entering and removing analytes to maximize the cross-validation rate, using information obtained from the univariate analyses and cross-validations. The final analyte classifier is then defined as the set of analyte predictors that gives the highest cross-validation rate.

Examples of data on the individual markers are discussed below, and are depicted in FIGS. 9-26. In most of the figures, data from individual subjects is shown as a dot, and the median and $5^{th}$ and $95^{th}$ percentiles are indicated by lines. This is adjacent in each case to lines indicating the mean and standard deviation for each group.

BDNF: BDNF has been suggested to play a role in depression. BDNF levels are reduced in depressed patients as compared to controls, and antidepressant treatment has been shown to increase serum BDNF levels in depressed patients. The level of plasma BDNF also can be increased with electroconvulsive therapy, suggesting that non-drug therapy can modulate BDNF levels (Marano et al. (2007) *J. Clin. Psych.* 68:512-7). As described above and shown in FIG. 9, the mean level of BDNF in the MDD group (17.76±5.27 ng/ml) was lower than the normal subject group (23.06±5.45), with a p value of 0.029. While univariate analysis identified BDNF as a marker with statistical significance, however, the ranges of BDNF levels for the two groups overlap significantly, indicating that serum BDNF by itself is not a good predictor of MDD.

Figure 11:
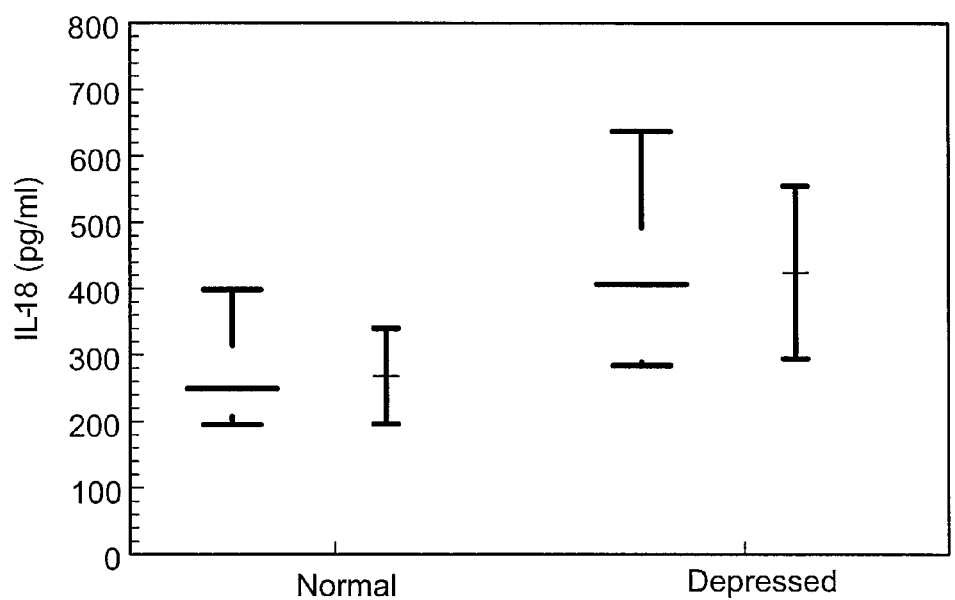
FIG. 11 is a graph plotting serum IL-18 levels in normal male subjects and male MDD patients. At left for each group are the median and the 5 and 95 percentile whiskers. The adjacent lines indicate the means and the standard deviations from the mean.

Interleukin 18: Psychological and physical stresses have been reported to exacerbate auto-immune and inflammatory diseases. Plasma concentrations of IL-18 have been shown to be significantly elevated in patients with major depression disorder or panic disorder as compared with normal controls. The elevation of plasma IL-18 levels may reflect increased production and release of IL-18 in the central nervous system under stressful settings (see, e.g., Sekiyama (2005) *Immunity* 22:669-77). As shown in FIG. 11, the inventors confirmed that IL-18 levels are higher in MDD patients than in normal controls (p=0.0038). Although evaluating IL-18 provided some differentiation of depressed patients from control subjects, this single marker test does not have sufficient diagnostic discrimination power or the robustness to be used in clinical practice.

Figure 12:
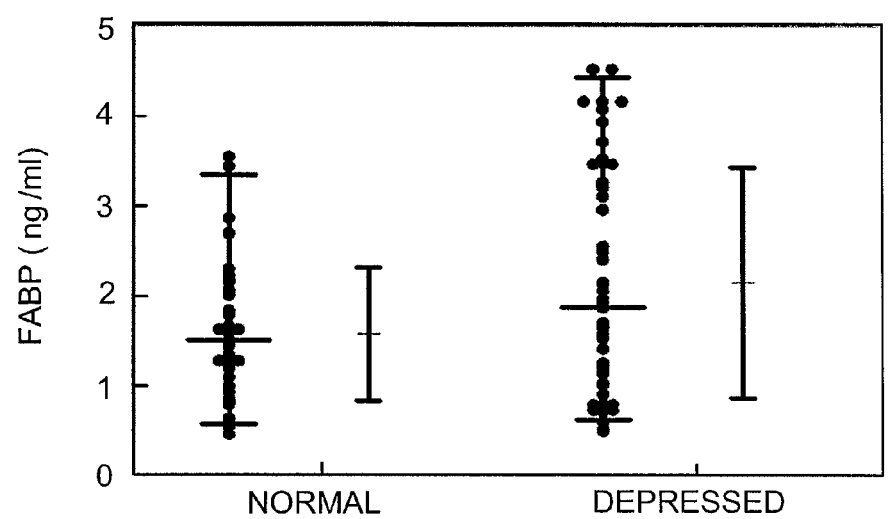
FIG. 12 is a graph plotting serum fatty acid binding protein (FABP) levels in normal male subjects and male MDD patients. The dots represent measurements for each subject, with the embedded median and the 5 and 95 percentile whiskers. The adjacent lines indicate the means and the standard deviations from the mean.

Fatty Acid Binding Protein: The brain is highly enriched in long-chain polyunsaturated fatty acids (PUFAs), which play important roles in brain structural and biologic functions. Plasma transport, in the form of free fatty acids or esterified FAs in lysophosphatidylcholine and lipoproteins, and de-novo synthesis contribute to brain accretion of long-chain PUFAs. docosahexaenoic acid (DHA) is an antidepressant (Mischoulon and Fava (2000) *Psychiatr. Clin. North Am.* 23:785-94), and FABP has been shown to be elevated in stroke and neurodegenerative diseases (Pelsers and Glatz (2005) *Clin. Chem. Lab. Med.* 43:802-809; and Zimmermann-Ivol et al. (2004) *Mol. Cell. Proteomics* 3:66-72.) As shown in FIG. 12, FABP was elevated in MDD patients as compared to controls (p=0.0056).

Figure 13:
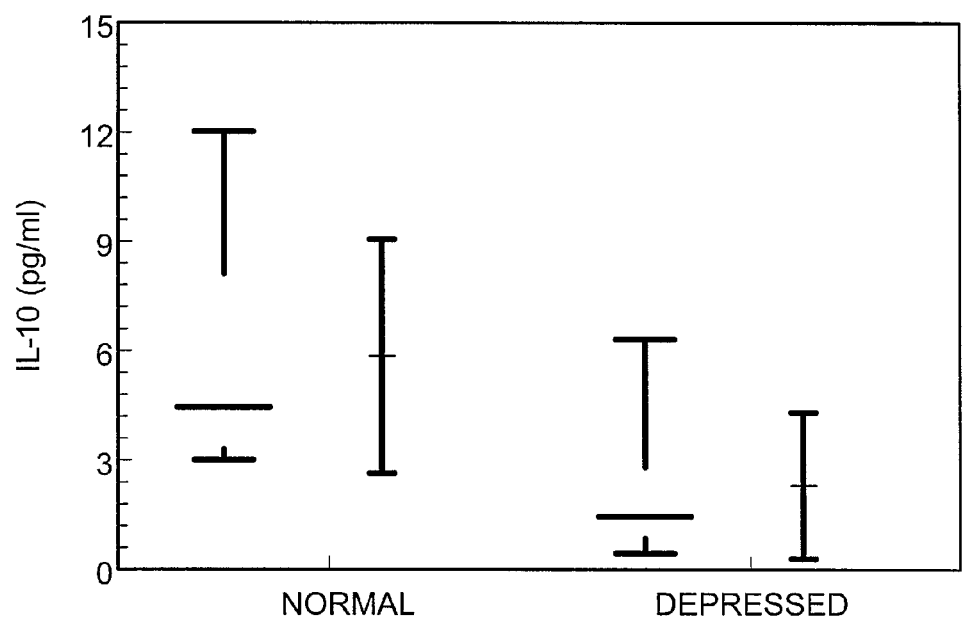
FIG. 13 is a graph plotting serum IL-10 levels in normal male subjects and male MDD patients. At left for each group are the median and the 5 and 95 percentile whiskers. The adjacent lines indicate the means and the standard deviations from the mean.

Interleukin 10: Depression is associated with activation of the inflammatory response system. Evidence suggests that pro-inflammatory and anti-inflammatory cytokine imbalance affects the pathophysiology of major depression. Pro-inflammatory cytokines are mainly mediated by T-helper (Th)-1 cells, and include IL-1β, IL-6, TNF-α, and interferon-γ. Anti-inflammatory cytokines are mediated by Th-2 cells, and include IL-4, IL-5, and IL-10. In humans, antidepressants significantly increase production of IL-10. As shown in FIG. 13, IL-10 levels were lower in plasma of MDD subjects as compared to controls (p=0.008).

Figure 14:
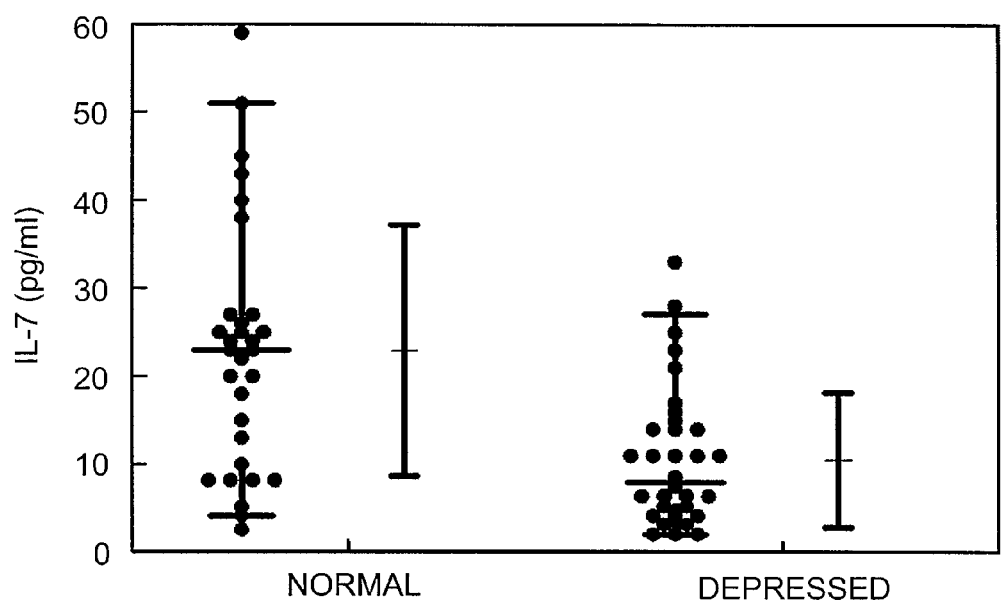
FIG. 14 is a graph plotting serum IL-7 levels in normal male subjects and male MDD patients. The dots represent measurements for each subject, with the embedded median and the 5 and 95 percentile whiskers. The adjacent lines indicate the means and the standard deviations from the mean.

Interleukin 7: Like IL-10, levels of IL-7 in plasma also were in reduced in depressed male subjects as compared to controls. IL-7 is a hematopoietic cytokine with critical functions in both B- and T-lymphocyte development. IL-7 also exhibits trophic properties in the developing brain. The direct neurotrophic properties of IL-7 combined with the expression of ligand and receptor in developing brain suggest that IL-7 may be a neuronal growth factor of physiological significance during central nervous system ontogeny (Michealson et al. (1996) *Dev. Biol.* 179:251-263). Adult neurogenesis has been implicated in the etiology and treatment of depression. Elevated stress hormone levels, which are present in some depressed patients and can precipitate the onset of depression, reduce neurogenesis in animal models. Conversely, virtually all antidepressant treatments, including drugs of various classes, electroconvulsive therapy, and behavioral treatments, increase neurogenesis (Drew and Hen (2007) *CNS Neurol. Disord. Drug Targets* 6:205-218). As shown in FIG. 14, IL-7 levels were reduced in MMD patients as compared to normal controls ($p=2.8e^{-5}$).

Figure 15:
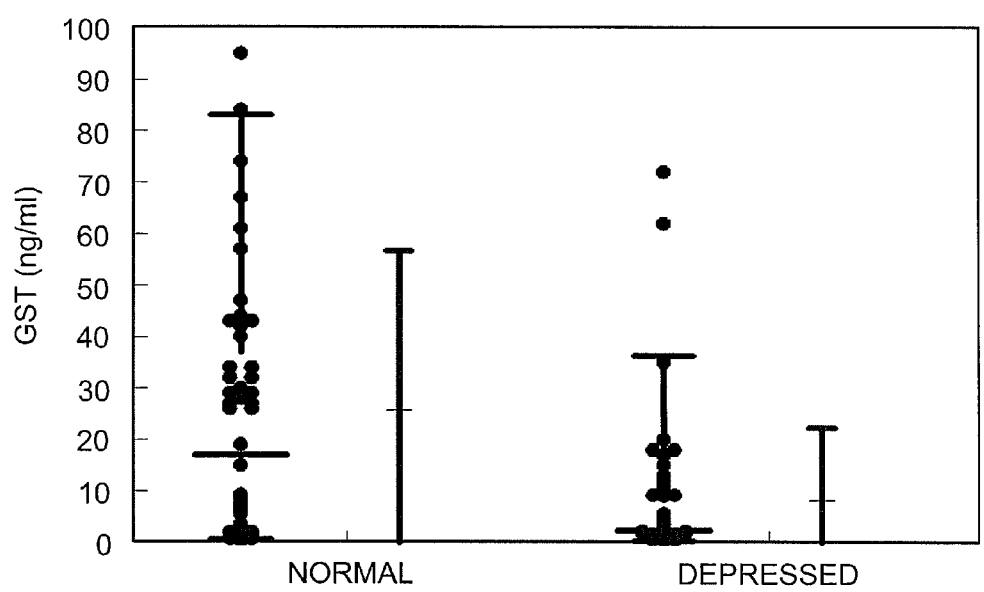
FIG. 15 is a graph plotting serum glutathione S-transferase (GST) levels in normal male subjects and male MDD patients. The dots represent measurements for each subject, with the embedded median and the 5 and 95 percentile whiskers. The adjacent lines indicate the means and the standard deviations from the mean.

Glutathione S-Transferase: Tricyclic antidepressants are known to inhibit the activity of GST pi isolated from different regions of human brain (e.g., the parietal cortex, frontal cortex, and brain stem). The inhibitory effect depends more on chemical structure than on brain localization of the enzyme. Tricyclics bind nonspecifically to the effector site of GST. The inhibitory effect of tricyclic antidepressants on brain GST may decrease the efficiency of the enzymatic barrier that protects the brain against toxic electrophiles, and may contribute in their adverse effects. On the other hand, brain GST may decrease the therapeutic effects of tricyclic antidepressants by binding them as ligands (Baranczyk-Kuzma et al. (2001) *Pol. Merkur Lekarski* 11:472-475.) As depicted in FIG. 15, mean levels of GST in the plasma of MDD subjects was reduced as compared to normal controls ($p=0.00047$).

Figure 16:
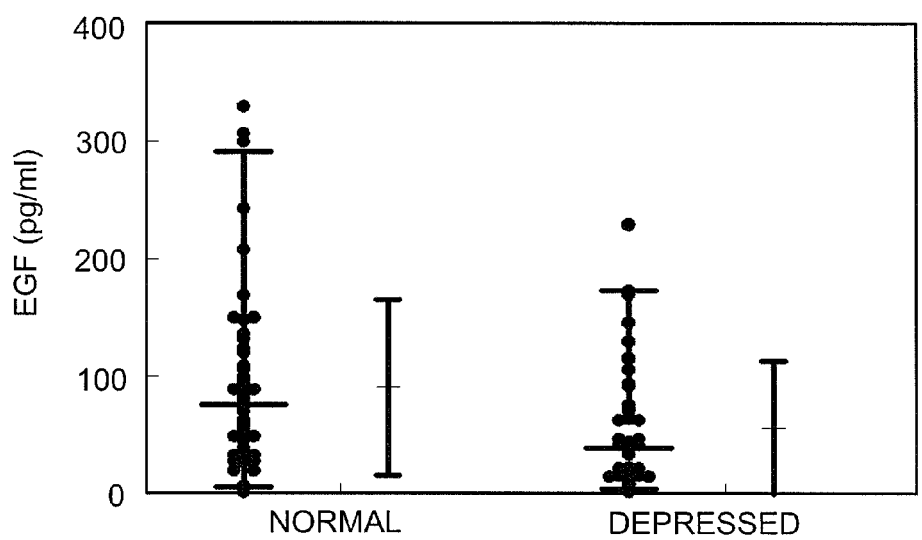
FIG. 16 is a graph plotting serum epidermal growth factor (EGF) levels in normal male subjects and male MDD patients. The dots represent measurements for each subject, with the embedded median and the 5 and 95 percentile whiskers. The adjacent lines indicate the means and the standard deviations from the mean.

EGF: Among the different factors that may be involved in neuroplasticity, glial cells use growth factor members of the EGF family, acting via receptors endowed with tyrosine kinase activity, to produce morphological changes and release neuroactive substances that directly excite nearby neurons. Agonists of tyrosine-kinase receptors (e.g., NGF, EGF, and basic FGF) enhance Na$^+$-dependent serotonin uptake in the synaptosomal-enriched P(2) fraction from rat-brain (Gil et al. (2003) *Neurochem. Int.* 42:535-542). As shown in FIG. 16, serum levels of EGF were decreased in MDD as compared to normal controls ($p=0.01$).

IL-13: IL-13 typically acts as an anti-inflammatory cytokine, suggesting that a lower level of IL-13 might increase the dysregulation of the immune system, resulting in increased proinflammatory cytokine activity. Systemic administration of the bacterial endotoxin lipopolysaccharide (LPS) has profound depressive effects on behavior that are mediated by inducible expression of proinflammatory cytokines such as IL-1, IL-6, and tumor necrosis factor-alpha (TNF-alpha) in the brain. When both LPS and IL-13 were co-injected, IL-13 potentiated the depressive effect (Bluthe et al. (2001) *Neuroreport* 12:3979-3983). As shown in FIG. 10, IL-13 levels were lower in depressed subjects than in normal controls ($p=1.2e^{-6}$).

Figure 17:
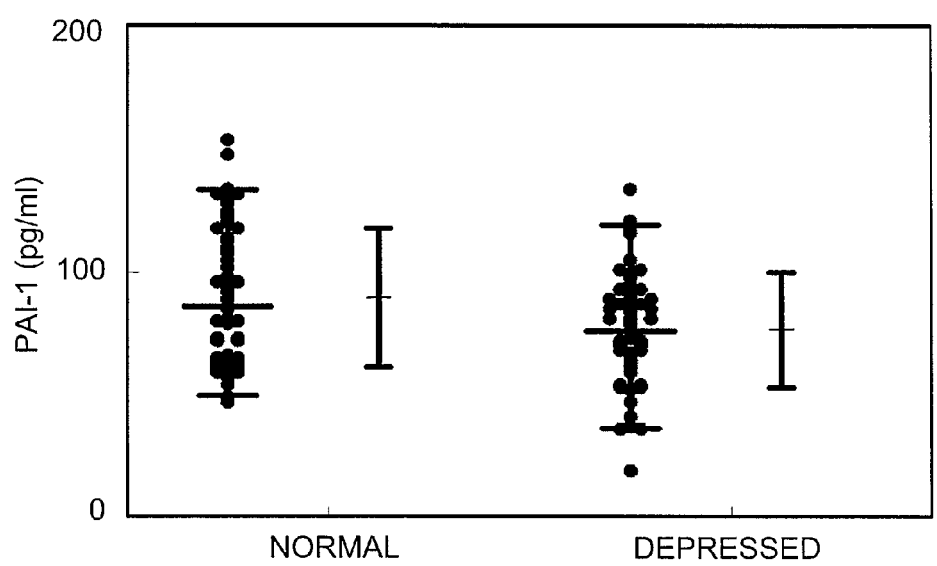
FIG. 17 is a graph plotting serum plasminogen activator inhibitor-1 (PAI-1) levels in normal male subjects and male MDD patients. The dots represent measurements for each subject, with the embedded median and the 5 and 95 percentile whiskers. The adjacent lines indicate the means and the standard deviations from the mean.

PAI-1: Tissue-type plasminogen activator (tPA) is a highly specific serine proteinase that catalyses the generation of zymogen plasminogen from the proteinase plasmin. Proteolytic cleavage of proBDNF, a BDNF precursor, to BDNF by plasmin represents a mechanism by which BDNF action is controlled. Furthermore, studies using mice deficient in tPA has demonstrated that tPA is important for the stress reaction, a common precipitating factor for MDD. Serum levels of the PAI-1, the major inhibitor of tPA, have been shown to be higher in women with MDD than in normal controls. See, e.g., Tsai (2006) *Med. Hypotheses* 66:319-322). As shown in FIG. 17, however, the inventors found that PAI-1 levels were lower in the serum of depressed male subjects as compared to normal controls ($p=0.01$).

Figure 18:
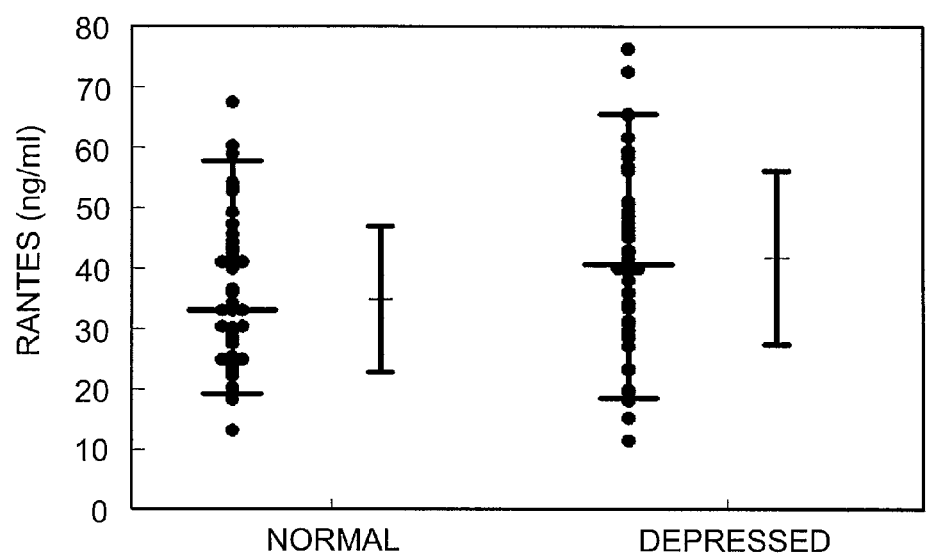
FIG. 18 is a graph plotting serum RANTES levels in normal male subjects and male MDD patients. The dots represent measurements for each subject, with the embedded median and the 5 and 95 percentile whiskers. The adjacent lines indicate the means and the standard deviations from the mean.

RANTES: Regulated upon Activation, Normal T-cell Expressed, and Secreted (RANTES; also known as CCL5) is an 8 kDa protein classified as a chemotactic cytokine or chemokine RANTES is chemotactic for T cells, eosinophils and basophils, and plays an active role in recruiting leukocytes into inflammatory sites. The combined effects of RANTES may serve to amplify inflammatory responses within the central nervous system (Luo et al. (2002) *Glia* 39:19-30). As shown in FIG. 18, serum levels of RANTES were elevated in subjects with MDD as compared to normal controls ($p=0.007$).

Figure 19:
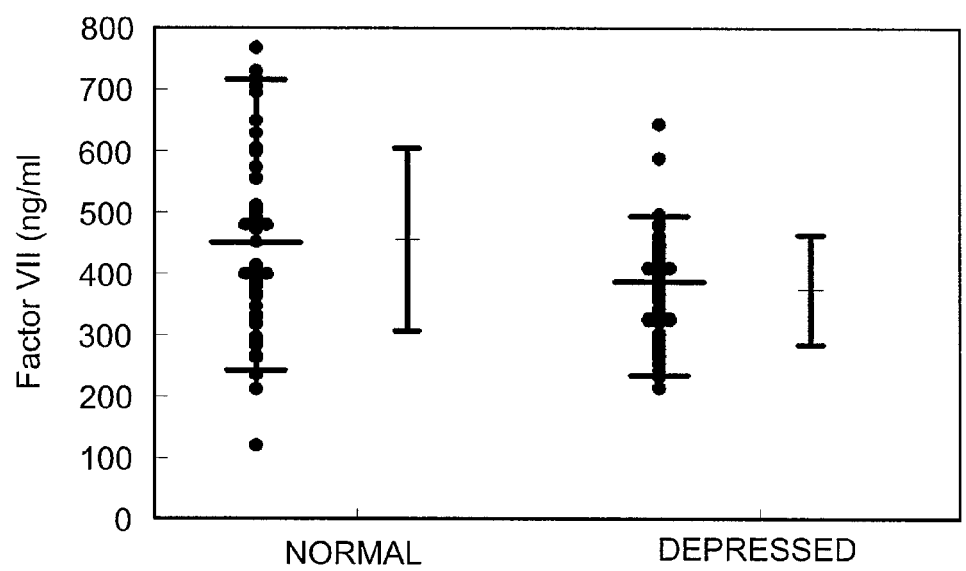
FIG. 19 is a graph plotting serum factor VII levels in normal male subjects and male MDD patients. The dots represent measurements for each subject, with the embedded median and the 5 and 95 percentile whiskers. The adjacent lines indicate the means and the standard deviations from the mean.

Factor VII: Psychological stressors and depressive and anxiety disorders also are associated with coronary artery disease. Changes in blood coagulation, anticoagulant, and fibrinolytic activity may constitute psychobiological pathways that link psychological factors with coronary syndromes (von Kanel et al. (2001) *Psychosom. Med.* 63:531-544). As shown in FIG. 19, levels of Factor VII were found to be lower in subjects with MDD as compared to normal controls ($p=0.0007$). This finding is contrary to some reports of hypercoagulation in depressed patients, particularly those with cardiovascular problems. However, depression has been shown to be associated with inflammation and coagulation factors in cardiovascular disease-free people, suggesting a possible pathway that leads to an increased frequency of events of coronary heart disease in depressive individuals (Panagiotakos (2004) *Eur. Heart J.* 25:492-499).

Figure 20:
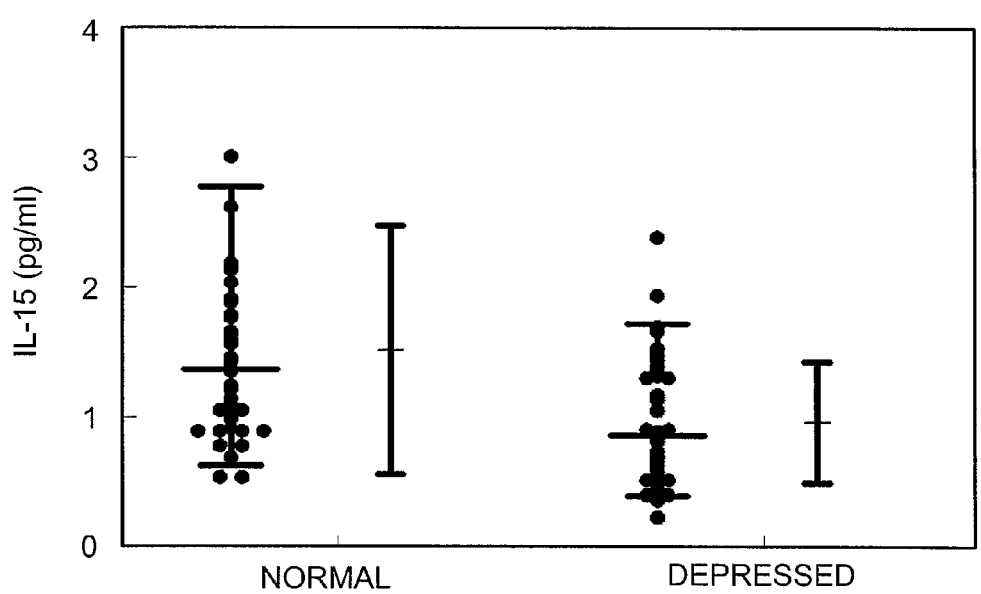
FIG. 20 is a graph plotting serum IL-15 levels in normal male subjects and male MDD patients. The dots represent measurements for each subject, with the embedded median and the 5 and 95 percentile whiskers. The adjacent lines indicate the means and the standard deviations from the mean.

IL-15: IL-15 is a proinflammatory cytokine that is involved in the pathogenesis of inflammatory/autoimmune disease. In addition, IL-15 has been shown to be somatogenic (Kubota et al. (2001) *Am. J. Physiol. Regul. Integr. Comp. Physiol.* 281: R1004-R1012). As shown in FIG. 20, IL-15 levels were lower in depressed subjects than in normal controls ($p=0.0005$).

Figure 21:
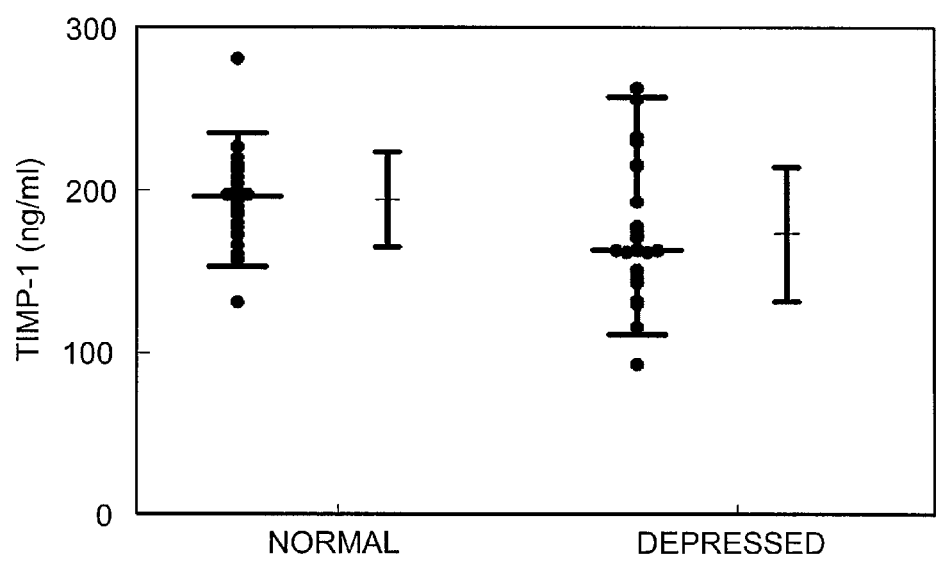
FIG. 21 is a graph plotting serum tissue inhibitor of matrix metalloproteinase-1 (TIMP-1) levels in normal male subjects and male MDD patients. The dots represent measurements for each subject, with the embedded median and the 5 and 95 percentile whiskers. The adjacent lines indicate the means and the standard deviations from the mean.

TIMP-1: Matrix metalloproteinases (MMPs) and the tissue inhibitors of metalloproteinases (TIMPs), whose expression can be controlled by cytokines, play a role in extracellular matrix remodeling in physiological and pathological processes. A positive association between plasma norepinephrine levels and MMP-2 protein levels, as well as a negative correlation between plasma cortisol levels and MMP-2 levels, has been observed (Yang et al. (2002) *J. Neuroimmunol.* 133:144-150). As shown in FIG. 21, TIMP-1 levels were significantly lower in depressed subjects than in normal controls ($p=0.038$).

Figure 22:
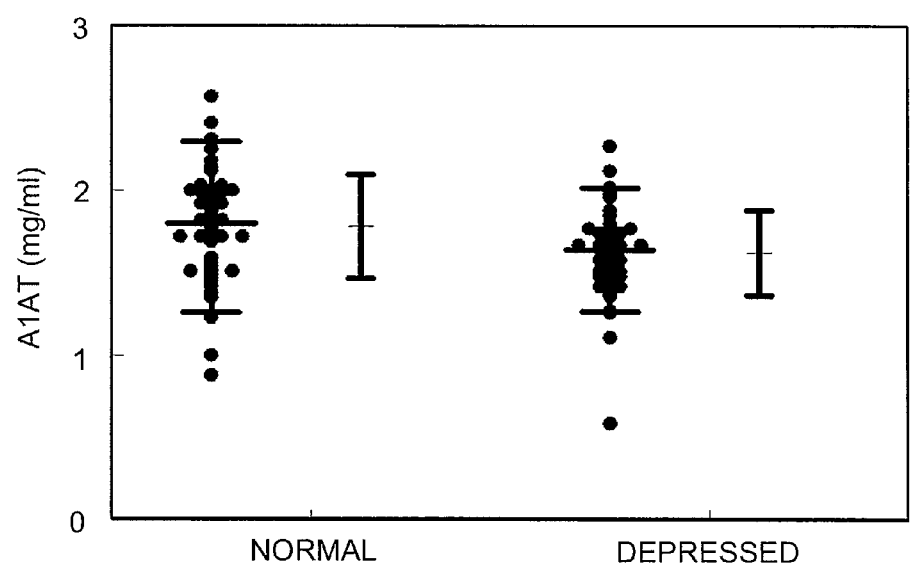
FIG. 22 is a graph plotting serum tissue inhibitor of alpha-1 antitrypsin (A1AT) levels in normal male subjects and male MDD patients. The dots represent measurements for each subject, with the embedded median and the 5 and 95 percentile whiskers. The adjacent lines indicate the means and the standard deviations from the mean.

Alpha-1 antitrypsin: Reduced activity of peptidases, such as prolylendopeptidase (PEP) and dipeptidyl peptidase IV (DPP IV), occurs in depression. As shown in FIG. 22, alpha-1 antitrypsin levels were lower in male subjects with depression than in normal controls ($p=0.0085$). This finding was in contrast to studies indicating that increased plasma concentrations of alpha-1 antitrypsin are found in severely depressed subjects as compared with healthy controls, with minor depressives exhibiting an intermediate position (Maes (1992) *J. Affect. Disord.* 24:183-192). It is possible that the MDD populations used in the present studies included significantly more moderate depressives.

Figure 23:
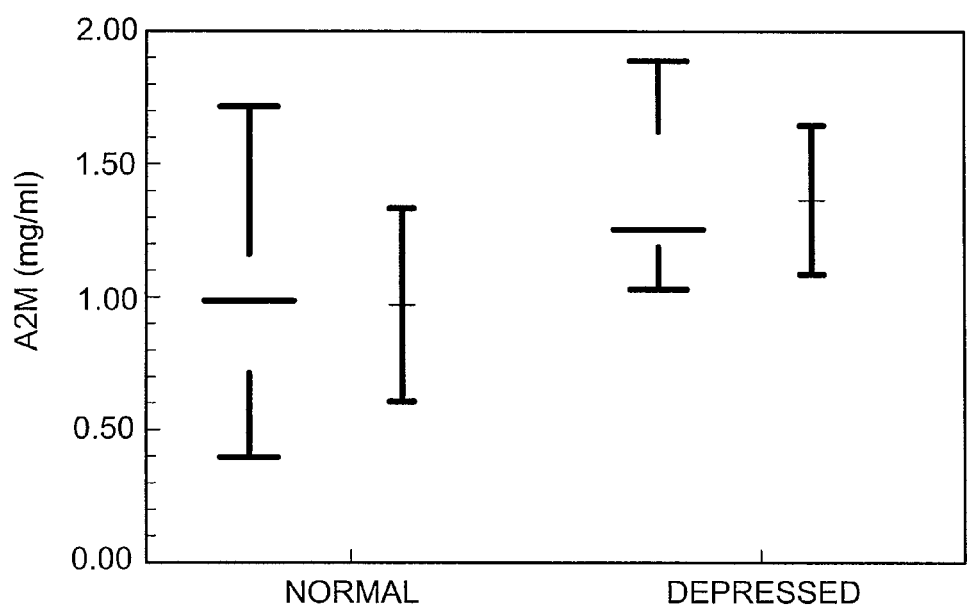
FIG. 23 is a graph plotting serum tissue inhibitor of alpha-2 macroglobulin (A2M) levels in normal male subjects and male MDD patients. At left for each group are the median and the 5 and 95 percentile whiskers. The adjacent lines indicate the means and the standard deviations from the mean.

A2M: A2M is a serum pan-protease inhibitor and an acute phase protein that has been associated with inflammatory disease. A2M also has been implicated in Alzheimer disease based on its ability to mediate the clearance and degradation of A beta, the major component of beta-amyloid deposits. Non-melancholic depressive patients have showed increased A2M serum concentrations in the acute stage of disease and after 2 and 4 weeks of treatment (Kirchner (2001) *J. Affect. Disord.* 63:93-102). Consistent with this finding, MDD patients were found to have increased levels of serum A2M than normal controls (p=0.0024; FIG. 23). In the present studies, there was no attempt to segregate melancholic from non-meloncholic patients.

Figure 24:
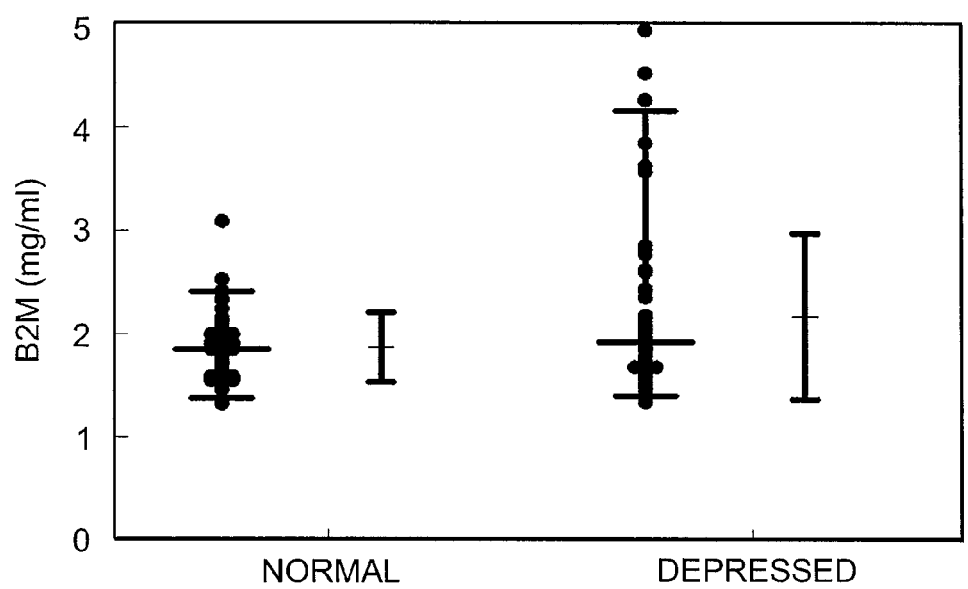
FIG. 24 is a graph plotting serum beta-2 macroglobulin (B2M) levels in normal male subjects and male MDD patients. The dots represent measurements for each subject, with the embedded median and the 5 and 95 percentile whiskers. The adjacent lines indicate the means and the standard deviations from the mean.

Beta 2 Microglobulin (B2M): B2M is a small (99 amino acid) protein that plays a key role in immunological defense. B2M can be modified by removal of the lysine at position 58, leaving the protein with two disulfide-linked chains of the amino acids 1-57 and 59-99. This modified form (desLys-58-β2-microglobulin, or ΔK58-β2m) has been shown to be associated with chronic inflammatory conditions (Nissen (1993) *Danish Med. Bul.* 40:56-64). B2M has been found to correlate with disease activity in several autoimmune disorders, and is used as a pharmacodynamic marker of interferon beta treatment in multiple sclerosis. As shown in FIG. 24, B2M levels were elevated in serum from MDD patients as compared to normal controls (p=0.013).

Figure 25:
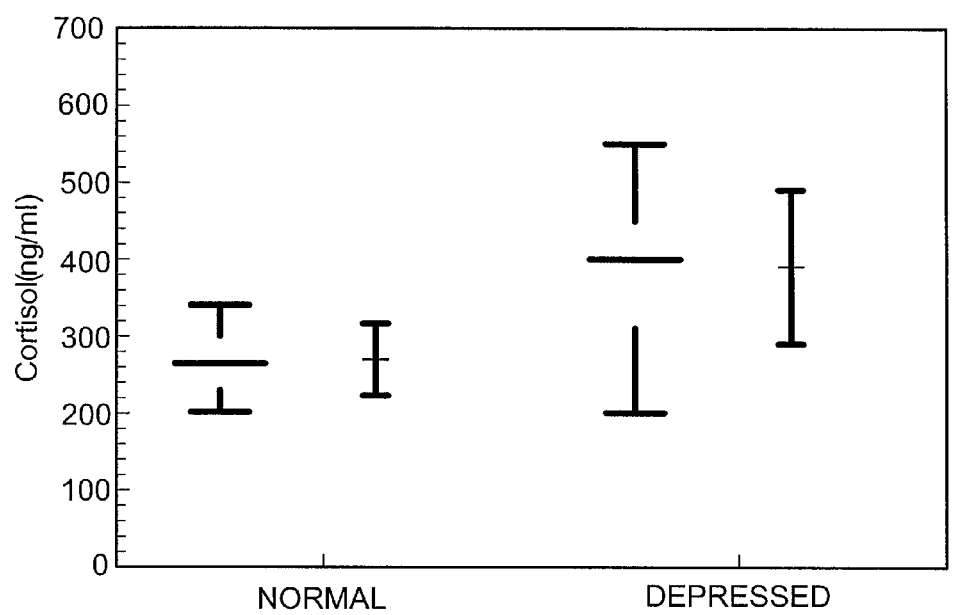
FIG. 25 is a graph plotting serum cortisol levels in normal male subjects and male MDD patients. The median and 5 and 95 percentile whiskers are shown at the left of each data set, while the adjacent lines to the right indicate the mean and standard deviations from the mean.

Cortisol: Cortisol is a corticosteroid hormone produced by the adrenal cortex of the adrenal gland. Cortisol is a vital hormone that is often referred to as the "stress hormone," as it is involved in the response to stress. This hormone increases blood pressure and blood sugar levels, and has an immunosuppressive action. Cortisol inhibits secretion of corticotropin-releasing hormone (CRH), resulting in feedback inhibition of ACTH secretion. This normal feedback system may break down when humans are exposed to chronic stress, and may be an underlying cause of depression. Hypercortisolism in depression has been reported, as reflected by elevated mean 24-hour serum cortisol concentrations and increased 24-hour urinary excretion of cortisol. In addition, prolonged hypercortisolemia may be neurotoxic, and recurrent depression episodes associated with elevated cortisol may lead to progressive brain damage. As shown in FIG. 25, cortisol levels in normal subjects (269±46.7 pg/ml) were significantly lower than in subjects with MDD (390±100.4 pg/ml; p=0.0028).

Figure 26:
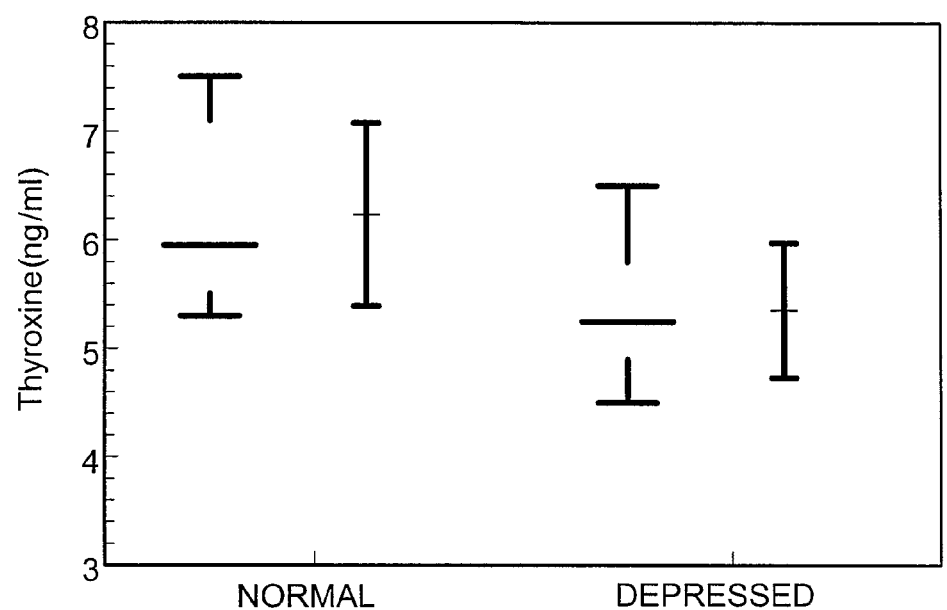
FIG. 26 is a graph plotting serum thyroxine levels in normal male subjects and male MDD patients. The median and 5 and 95 percentile whiskers are shown at the left of each data set, while the adjacent lines to the right indicate the mean and standard deviations from the mean.

Thyroxine ($T_4$): $T_4$ is involved in controlling the rate of metabolic processes in the body and influencing physical development. The thyroid gland and thyroid hormones generally are believed to be important in the pathogenesis of major depression. For example, studies have documented alterations in components of the hypothalamic-pituitary-thyroid (HPT) axis in patients with primary depression. Screening thyroid tests, however, often add little to diagnostic evaluation, and overt thyroid disease is rare among depressed inpatients. The finding that depression can co-exist with autoimmune subclinical thyroiditis suggests that depression may cause alterations in the immune system, or that it could be an autoimmune disorder itself. The outcome of treatment and the course of depression may be related to thyroid status as well. Augmentation of antidepressant therapy with co-administration of thyroid hormones (mainly $T_3$) is a treatment option for refractory depressed patients. As shown in FIG. 26, thyroxine levels in normal subjects (6.23±0.842 ng/ml) were higher than in subjects with MDD (5.35±0.622 ng/ml; p=0.016).

Figure 27:
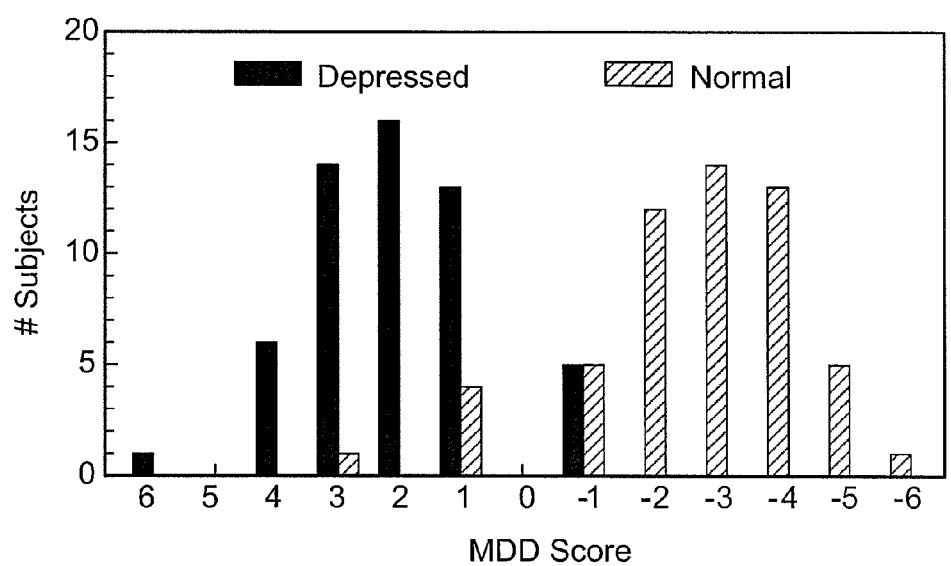
FIG. 27 is a graph plotting the results of partial least squares discriminant analysis (PLS-DA) of sera from control (striped bars) and MDD (solid bars) patients, which were determined using a biomarker library panel of about 85 serum protein analytes to quantify 16 markers: BDNF, IL-7, IL-10, IL-13, IL-15, IL-18, FABP, adrencorticotropic hormone (ACTH), thyroxine, factor VII, EGF, A2M, GST, RANTES, TIMP-1, and PAI-1.

Using 15 of the markers listed above (IL-7, IL-10, IL-13, IL-15, IL-18, BDNF, FABP, GST, EGF, RANTES, TIMP-1, A1AT, PAI-1, factor VII, and $T_4$), as well as ACTH, a diagnostic score was established based on the following algorithm:

Depression diagnosis score=f(a1*analyte1+a2*analyte2+ a3*analyte3+a4*analyte4+a5*analyte5+a6*analyte6+ a7*analyte7+a8*analyte8+a9*analyte9+a10*analyte10+ a11*analyte11+a12*analyte12+a13*analyte13+ a14*analyte14+a15*analyte15+a16*analyte16). More specifically, a depression score was assigned to each subject using PLS-DA. The depression diagnostic score for each subject was calculated, and the results are plotted in FIG. 27.

The scores were determined statistically to have a sensitivity >90% and a specificity >85%.

Using five of the markers listed above (A2M, BDNF, IL-10, IL-13, and IL-18), a diagnostic score was established based on the following algorithm:

Depression diagnosis score=f(a1*analyte1+a2*analyte2+ a3*analyte3+a4*analyte4+a5*analyte5).

Here, a1, a2, a3, a4, and a5 are the B values shown in Table 4. The algorithm had a sensitivity of 86.3% and a specificity of 77.1%.

Several examples of depression algorithms using different marker sets were established and are shown in Tables 5-10. In particular, MDD algorithms with subsets of 4 analytes are shown in Table 5 (A2M, BDNF, IL-10, and IL-13), Table 6 (A2M, BDNF, IL 10, and IL-18), and Table 7 (A2M, BDNF, IL-13, and IL-18). Algorithms with subsets of 3 analytes are shown in Table 8 (A2M, BDNF, and IL-10), Table 9 (A2M, BDNF, and IL-13), and Table 10 (A2M, BDNF, and IL-18).

TABLE 4

Algorithm with A2M, BDNF, IL-10, IL-13, and IL-18

| | B | S.E. | Wald | df | Sig. | Exp(B) |
|---|---|---|---|---|---|---|
| A2M | .748 | .867 | .745 | 1 | .388 | 2.114 |
| BDNF | −.231 | 0.67 | 11.984 | 1 | .001 | .794 |
| IL-10 | −.457 | .151 | 9.208 | 1 | .002 | .633 |
| IL-13 | −.029 | .020 | 2.265 | 1 | .132 | .971 |
| IL-18 | 0.011 | .003 | 10.570 | 1 | .001 | 1.011 |
| Constant | 2.822 | 1.800 | 2.456 | 1 | .117 | 16.806 |

| | Predicted | | |
|---|---|---|---|
| | | Sick1 | Percentage |
| Observed | | 0    1 | correct |
| SICK1 | 0 | 37    11 | 77.1 |
| | 1 | 7    44 | 86.3 |
| Overall percentage | | | 81.8 |

TABLE 5

Algorithm with A2M, BDNF, IL-10, and IL-13

| | B | S.E. | Wald | df | Sig. | Exp(B) |
|---|---|---|---|---|---|---|
| A2M | .739 | .787 | .883 | 1 | .347 | 2.095 |
| BDNF | −.161 | 0.55 | 8.551 | 1 | .003 | .851 |
| IL-10 | −.206 | .110 | 3.521 | 1 | .061 | .814 |
| IL-13 | −.048 | .017 | 8.025 | 1 | .005 | .954 |
| Constant | 4.254 | 1.625 | 6.854 | 1 | .009 | 70.405 |

| | Predicted | | |
|---|---|---|---|
| | | Sick1 | Percentage |
| Observed | | 0    1 | correct |
| SICK1 | 0 | 32    16 | 66.7 |
| | 1 | 11    40 | 78.4 |
| Overall percentage | | | 72.7 |

TABLE 6

Algorithm with A2M, BDNF, IL-10, and IL-18

| | B | S.E. | Wald | df | Sig. | Exp(B) |
|---|---|---|---|---|---|---|
| A2M | .922 | .871 | 1.122 | 1 | .290 | 2.515 |
| BDNF | −.228 | .065 | 12.152 | 1 | .000 | .796 |
| IL-10 | −.553 | .137 | 16.275 | 1 | .000 | .575 |

TABLE 6-continued

Algorithm with A2M, BDNF, IL-10, and IL-18

| | B | S.E. | Wald | df | Sig. | Exp(B) |
|---|---|---|---|---|---|---|
| IL-18 | 0.13 | .003 | 13.999 | 1 | .000 | 1.013 |
| Constant | 1.973 | 1.695 | 1.355 | 1 | .244 | 7.190 |

| | | Predicted | | |
|---|---|---|---|---|
| | | Sick1 | | Percentage |
| Observed | | 0 | 1 | correct |
| SICK1 | 0 | 36 | 12 | 75.0 |
| | 1 | 10 | 41 | 80.4 |
| Overall percentage | | | | 77.8 |

TABLE 7

Algorithm with A2M, BDNF, IL-13, and IL-18

| | B | S.E. | Wald | df | Sig. | Exp(B) |
|---|---|---|---|---|---|---|
| A2M | 1.148 | .824 | 1.941 | 1 | .164 | 3.151 |
| BDNF | −.165 | .057 | 8.336 | 1 | .004 | .848 |
| IL-13 | −.058 | .016 | 12.308 | 1 | .000 | .944 |
| IL-18 | .007 | .003 | 5.894 | 1 | .015 | 1.007 |
| Constant | 1.486 | 1.637 | .824 | 1 | .364 | 4.419 |

| | | Predicted | | |
|---|---|---|---|---|
| | | Sick1 | | Percentage |
| Observed | | 0 | 1 | correct |
| SICK1 | 0 | 33 | 15 | 68.8 |
| | 1 | 10 | 42 | 80.8 |
| Overall percentage | | | | 75.0 |

TABLE 8

Algorithm with A2M, BDNF, and IL-10

| | B | S.E. | Wald | df | Sig. | Exp(B) |
|---|---|---|---|---|---|---|
| A2M | 1.209 | .755 | 2.563 | 1 | .109 | 3.351 |
| BDNF | −.139 | .049 | 7.986 | 1 | .005 | .781 |
| IL-10 | −.345 | .102 | 11.318 | 1 | .001 | .708 |
| Constant | 2.994 | 1.403 | 4.550 | 1 | .033 | 19.956 |

| | | Predicted | | |
|---|---|---|---|---|
| | | Sick1 | | Percentage |
| Observed | | 0 | 1 | correct |
| SICK1 | 0 | 36 | 12 | 75.0 |
| | 1 | 13 | 38 | 74.5 |
| Overall percentage | | | | 74.7 |

TABLE 9

Algorithm with A2M, BDNF, and IL-13

| | B | S.E. | Wald | df | Sig. | Exp(B) |
|---|---|---|---|---|---|---|
| A2M | 1.009 | .781 | 1.670 | 1 | .196 | 2.744 |
| BDNF | −.137 | .052 | 7.019 | 1 | .008 | .872 |
| IL-13 | −.059 | .016 | 14.652 | 1 | .000 | .942 |
| Constant | 3.083 | 1.444 | 4.560 | 1 | .033 | 21.832 |

TABLE 9-continued

Algorithm with A2M, BDNF, and IL-13

| | | Predicted | | |
|---|---|---|---|---|
| | | Sick1 | | Percent-age |
| Observed | | 0 | 1 | correct |
| SICK1 | 0 | 32 | 16 | 66.7 |
| | 1 | 11 | 41 | 78.8 |
| Overall percentage | | | | 73.0 |

TABLE 10

Algorithm with A2M, BDNF, and IL-18

| | B | S.E. | Wald | df | Sig. | Exp(B) |
|---|---|---|---|---|---|---|
| A2M | 2.111 | .763 | 7.652 | 1 | .006 | 8.261 |
| BDNF | −.117 | .047 | 6.319 | 1 | .012 | .889 |
| IL-18 | .007 | .003 | 8.205 | 1 | .004 | 1.007 |
| Constant | −1.691 | 1.258 | 1.807 | 1 | .179 | .184 |

| | | Predicted | | |
|---|---|---|---|---|
| | | Sick1 | | Percentage |
| Observed | | 0 | 1 | correct |
| SICK1 | 0 | 35 | 13 | 72.9 |
| | 1 | 12 | 40 | 76.9 |
| Overall percentage | | | | 75.0 |

Further Studies

A number of questions have been raised about serum markers for neuropsychiatric diseases. For example, previous studies investigating testosterone levels and mood disorders showed conflicting results. In the present studies, however, no significant differences were noted between levels of testosterone in 12 depressed males as compared to age-matched normal controls.

Similarly, in a study of depressed psychiatric inpatients and normal controls, platelet serotonin (blood serotonin) content was significantly higher among depressed psychiatric inpatients with a recent case of a mood disorder than among depressed psychiatric inpatients without recent history of mood disorder. Other results suggested that depressed patients with abnormal personality disorder had higher levels of platelet serotonin than patients without personality disorder. In addition to similarities between 5-HT2A serotonin receptors in platelets and brain, levels of serotonin transporter (SERT) in platelet membranes are identical to those found in the CNS. A number of studies have shown a reduction in SERT density in platelets of depressed individuals compared to SERT density in platelets of healthy subjects.

More often than not, results from a single assay, or a group of assays considered as single assays rather than an algorithm, do not provide valuable information about a single patient. For example, a number of studies have indicated that BDNF is lower in depressed patients as compared to controls. Indeed, several studies have demonstrated that antidepressants increase BDNF levels, and that activating the BDNF-signaling pathway may play an important role in their therapeutic mechanism. FIG. 9 shows the levels of serum BDNF in the AJ male population ($p=0.029$ for depressed vs. controls). One of the critical aspects of any sample set is the documentation available. Since many samples are taken for reasons other than plasma protein phenotyping, the data relevant to the time of day and the last time the patient took any medication is often missing. It should be pointed out, however, that while there was variation in when the individual blood samples analyzed herein were drawn, perhaps leading to increased patient variation, the samples were taken during normal working hours so that marked changes due to diurnal variation would not be expected.

An expanded library of antibodies (PHB's highly multiplexed screening technology, with a capacity of about 200 markers) is extended to samples (e.g., plasma or serum) from well-characterized patients. Antibodies for proteins of interest (e.g., monoamines and thyroid hormones) are evaluated. Markers associated with neuropsychiatric disease also are evaluated (e.g., in collaboration with academic laboratories doing mass spectroscopy-based discovery in CSF from depressed subjects).

Since the initial studies were limited with regard to antidepressant naïve subjects, patients who are antidepressant naïve are identified for the extension studies. Such subjects are imaged with magnetic resonance spectroscopy, including phosphorus magnetic resonance spectroscopy ($^{31}$P-MRS) studies. Studies have suggested that cerebral metabolic changes are implicated in the pathology of MDD. Experiments using $^{31}$P-MRS have shown that cerebral energy metabolism [e.g., beta-nucleoside triphosphate (beta-NTP), primarily reflecting brain levels of adenosine triphosphate (ATP)] is lower in depressed subjects than in normal controls, and is positively correlated with severity of depression. Beta-NTP levels also appear to correct after successful antidepressant treatment, but not in treatment of non-responders. The $^{31}$P-MRS methods described herein include 3D chemical shift imaging and the possibility to measure $^{31}$P-MRS metabolites from specific brain regions. Inclusion-exclusion criteria, study design, randomization and treatment, as well as specific instruments to be used for clinical characterization of subjects are determined using standard protocols.

The sensitivity and specificity of custom protein arrays for determination of multiple biomarkers from blood, sera, cerebrospinal fluid, and/or urine are determined. In addition, appropriate algorithms are developed that reflect concordance between protein signatures and imaging, as well as psychological testing.

The antibody arrays are designed to provide a fast, reliable, high-throughput, sensitive, and quantitative detection tool for multiple differentially expressed antigens (including annotated proteins and post-translationally modified proteins, for example) from a limited amount of sample (e.g., 20 to 50 µl of serum). Surfaces and array designs are developed to be compatible with samples obtained through a minimally invasive method in order to provide the opportunity for sequential sampling. Sera or plasma typically are used, but, as indicated herein, other biological samples also may be useful. For example, specific monoamines can be measured in urine. In addition, depressed patients as a group have been found to excrete greater amounts of catecholamines (CAs) and metabolites in urine than healthy control subjects. Analytes of interest include, for example, norepinephrine, epinephrine, vanillylmandelic acid (VMA), and 3-methoxy-4-hydroxyphenylglycol (MHPG). Proteomic studies have indicated that urine is a rich source of proteins and peptides that may be differentially expressed in disease states.

While the initial study focused on males, the findings are extended to women, since after puberty women are twice as likely as men to develop depression. Since estrogen may be associated with some of the age-related changes in mood (e.g., post-partum depression, or depression in the perimenopausal period) estrogen levels are concomitantly measured in studies of female subjects.

Example 2

Diagnostic Markers of Cancer

An algorithm is developed to determine diagnostic/prognostic scores for cancer (e.g., breast cancer). Breast cancer is the most common female cancer in the United States, the second most common cause of cancer death in women (after lung cancer), and the main cause of death in women ages 45 to 55. Every year, approximately 205,000 American women are diagnosed with breast cancer, and more than 40,000 die from it. Early detection is a major factor contributing to the 3.2% annual decline in breast cancer death rates over the past 5 years. Unfortunately, currently available breast cancer screening tools such as mammography and breast examination miss up to 40% of early breast cancers and are least effective in detecting cancer in young women, whose tumors are often more aggressive.

Breast cancers are classified histologically based upon the types and patterns of cells from which they are composed. Carcinomas can be invasive (extending into the surrounding stroma) or non-invasive (confined just to the ducts or lobules). Histologic features and breast cancer grade have been correlated with expression of receptors such as Her2/neu, estrogen receptor (ER), and progesterone receptor (PR). For example, overexpression of HER2, p53, vascular endothelial growth factor (VEGF), and cyclin E proteins in primary tumors has been shown to predict increased risk for metastatic disease and decreased survival, while expression of ER and PR are associated with favorable outcomes. While these and other antigens (e.g., Ki67, p53, and bcl-2) may correlate with tumor grade, they do not appear to be independent prognostic factors. Other factors have been found to play a role in the complex progression of ductal carcinoma in situ (DCIS), including extracellular matrix regulation and degradation, cell cycle regulation, angiogenesis, and mitogenesis factors. Comprehensive analysis is not always possible, given the complexity of the disease, the number of potential markers, the invasiveness of the procedure, restricted access to sequential samples and limited tissue obtained by needle biopsy, and the potential cost. Nonetheless, recent developments in gene and proteomic profiling of pre-cancerous and cancerous lesions suggest that patterns of markers may be useful as a holistic phenotype of an individual's disease and response.

To date, only ER and PR status are accepted predictors for responsiveness, and are used in clinical decision making for adjuvant endocrine treatment. There is a dearth of soluble biomarkers that can be detected from serum both pre- and post-operatively. Given the importance of early diagnosis, staging and monitoring therapy, the development of noninvasive techniques to aid in detection of cancer and determination of prognosis is of crucial importance.

Serum or other body fluid markers in addition to ER and PR are utilized for diagnosis and monitoring. Access to the markers utilized in the methods described herein is obtained through, for example, interactions with academic, government, and industry laboratories. It is noted, however, that the platform remains flexible and open to the addition of new analytes. Potential additional markers include the following.

ErbB-2: Human-epidermal-growth-factor receptor 2 (ErbB-2, p185HER2) is a transmembrane glycoprotein with an intracellular tyrosine kinase activity and an extracellular domain similar to those of the EGF-binding domain of the EGF receptor. The use of ErbB2 as a marker for response to therapy is controversial, although the extracellular domain (ECD) of the ErbB-2 protein is frequently cleaved and released into the circulation, where it can be detected by ELISA in about 45% of patients with metastatic breast cancer. Increased serum HER2/neu concentrations have been associated with progressive metastatic disease, as well as and poor response to chemotherapy and hormonal therapy. The inventors have developed an assay for ErbB-2, and have utilized the antibody pairs in a custom SearchLight™ multiplex.

CA-15-3: The CA 15-3 assay has had limited use in the management of stage II and III breast cancer patients. Patients with confirmed breast carcinoma frequently have CA 15-3 assay values in the same range as healthy individuals, and elevated levels can occur in subjects without malignant breast carcinoma. CA 15-3 thus may not be useful for monitoring, unless the marker is high at the time of initial treatment. Nonetheless, studies have indicated the utility of this marker for serial monitoring of patients. CA 15-3 levels can be used in conjunction with other clinical methods for monitoring breast cancer, and may be more useful in the context of a multiplex. Antibodies and assay kits are available for CA-15-3 detection in blood, and the assay can be adapted to the platforms utilized herein.

Mammaglobin: Mammaglobin is a 10 kDa glycoprotein that is distantly related to a family of epithelial secretory proteins such as the human Clara cell 10 kDa protein (CC10)/uteroglobin. Indeed, mammaglobin, a mammary-specific member of the uterglobin family, is overexpressed in human breast cancer and is detectable in sera of breast cancer patients.

Angiogenesis and proteins involved in tissue remodeling: Breast carcinoma, like most other solid tumors, needs to develop an angiogenic phenotype for invasiveness, progression and metastasis. VEGF levels in sera appear to be useful for staging patients, and therefore may be valuable for patient monitoring. In earlier studies, a SearchLight™ panel was developed that determined the levels of MMPs and TIMPs in sera.

Autoantibodies: It is known that sera from breast and other cancers contain antibodies that react with tumor-associated antigens. Although these antibodies occur relatively infrequently and have low affinity low affinity for known tumor associated antigens, the label-free MIMS technology is particularly suitable to phenotyping an antibody response to a specific antigen (see, e.g., Notkins (2007) Sci. Amer. 71:72-79). The inventors have had modest success in printing both protein and peptide antigens on nanostructured chips and capturing specific antibody. A major advantage of the MIMS system is that a large number of antigens can be printed and rapidly optically scanned on the chip in the absence of secondary antibody. Both the pattern of autoantibodies expressed as well as quantitative changes in the amount of antibody detected over time (e.g., subsequent to radiation) can be measured by MIMS. In addition, since autoantibodies may appear in nipple aspirate fluid (NAF), it may be useful to measure autoantibodies in NAF for early detection or monitoring recurrence.

Example 3

Diagnostic Markers of Chronic Obstructive Pulmonary Disease (COPD)

COPD is a disease state characterized by airflow limitation that is not fully reversible. The clinical hallmark of COPD is an accelerated decline in lung function with aging. In most cases the airflow limitation represents, in part, an abnormal inflammatory response in the airways to noxious particles and gases (Pauwels et al. (2001) Am. J. Respir. Crit. Care Med. 163:1256-1276). COPD is recognized as a major global health issue that affects over 5% of the adult population, and is the only major cause of death in industrialized nations in which morbidity and mortality are increasing. Over the next twenty years, mortality due to COPD is expected to increase five-fold. The true health burden of COPD is underestimated, however, because airflow obstruction is an important contributor to other common causes of morbidity and mortality, including ischemic heart disease, stroke, pneumonia and lung cancer (Engstrom et al. (2001) Circulation 103:3086-3091; Sin and Mann (2005) Proc. Am. Thorac. Soc. 2:8-11; Mannino et al. (2003) Arch. Intern. Med. 163:1475-1480; and Hole et al. (1996) Brit. Med. J. 313:711-715).

COPD is a systemic disorder, the extrapulmonary manifestations of which involve diverse organs and include skeletal muscle dysfunction, muscle wasting, osteoporosis, and atherosclerosis and its associated complications. Weight loss in patients with COPD may be related to increased circulating levels of inflammatory mediators (e.g., tumor necrosis factor alpha and inflammatory cytokines). Importantly, there is a general association between the severity of the airflow obstruction and the severity of extrapulmonary end-organ damage in patients with COPD (Andreassen and Vestbo (2003) Eur. Respir. J. Suppl. 22:2s-4-s). The potential effects of COPD on the cardiovascular system are important clinically because data from large longitudinal studies of COPD patients indicate that the leading cause of hospitalization and mortality in established COPD patients is cardiovascular in nature (Anthonisen et al. (2002) Am. J. Respir. Crit. Care Med. 166:333-339; and Camilli et al. (1991) Am. J. Epidemiol. 133:795-800). Poor lung function has been shown to be as important a predictor of cardiac mortality as well established risk factors such as total serum cholesterol. How COPD increases the risk of poor cardiovascular outcomes is largely unknown, however. A potential mechanism is that pulmonary inflammation leads to systemic inflammation.

There is uncertainty and debate about the best way to screen for and diagnose COPD. Airflow restriction in COPD usually is progressive and associated with an abnormal inflammatory response in the lung. Airflow limitation is the slowing of expiratory airflow as measured by spirometry, with a consistently low forced expiratory volume in one second (FEV1) that can be reversed to some extent with inhaled corticosteroids or bronchodialators.

Although the degree of FEV1 impairment seen after bronchodilator inhalation is a fairly good prognostic marker in the study of COPD populations, the extent of FEV1 decreases do not correlate well with reduced quality of life in individual patients. A dyspnea index or a more complex index such as the BODE (including measures of dyspnea, exercise capacity, and systemic dysfunction such as weight loss (Celli et al. (2004) N. Engl. J. Med. 350:1005-1012)) correlates better with quality of life impairment. Changes in FEV1 occur slowly over the course of COPD, and such changes can be difficult to apply to clinical studies of new therapeutics.

Acute-on-chronic deteriorations of respiratory health in COPD are termed exacerbations. Exacerbations contribute to decline in lung function (Donaldson et al. (2002) Thorax 57:847-852), impairment to health status (Seemungal et al. (1998) Am. J. Respir. Crit. Care Med. 157:1418-1425), hospital admissions (Ashton et al. (1995) Q. J. Med. 88:661-672), and therefore healthcare costs and mortality (Soler-Cantalufia et al. (2005) Thorax 60:925-931). Patients who experience more than 2 exacerbations per year are especially difficult to manage. Several potential host, pathogen, and treatment factors have been identified that contribute to recurrent exacerbation. There is a substantial need, however, to understand the etiology and identify efficacious interventions to reduce the frequency of COPD exacerbations.

Results

Though there is debate as to whether the systemic manifestations of COPD are solely the result of the lung disease or if COPD is a systemic disease that mainly manifests in the lungs, changes in serum protein levels may be useful in diagnosis and treatment (Pinto-Plata et al. (2007) *Thorax* 62:595-601). In these studies, the final panel included multiple analytes that had a statistically significant correlation with FEV1, diffusing capacity of the lung for carbon monoxide (DLCO), six minute walk distance (6MWD), BODE scale, and exacerbation frequency, but no correlation with body mass index (BMI; Pinto-Plata et al. (2007) *Thorax* 62:595-601). From these studies, it was concluded that serum biomarkers can be useful in the diagnosis of COPD, and may be useful in future treatment strategies.

Further Studies

Based on earlier studies, a panel of analytes is developed into an array or arrays that provide an objective aid to identification and monitoring of patients with COPD, with emphasis on patient stratification and identification of frequent exacerbators. Custom antibody array(s) for about 25 to 50 antigens are designed, developed, and analytically validated in sera from well characterized patients from a single site. Algorithm(s) are then developed that reflect concordance between protein signatures and BODE score, in addition to spirometry. The algorithms are evaluated using investigator blinded test sets. This panel is initially developed on a Luminex or Pierce SearchLight™ technology platform, and then is transferred to PHB nanostructured chips.

The aforementioned panel of systemic biomarkers (Pinto-Plata et al. (2007) *Thorax* 62:595-601) was not useful in predicting exacerbation severity. Nonetheless, the acute-phase response at exacerbation was most strongly related to indices of monocyte function. Patient samples obtained pre- and post-exacerbation were heterogenous with regard to the causative agent, exacerbation frequency, and severity (Hurst et al. (2006) *Am. J. Respir. Crit. Care Med.* 174:867-874). Samples for further studies are better characterized with regard to the causative agent, and COPD severity is assessed by BODE score as well as spirometry.

Given the failure of the panel to predict exacerbation frequency, which is critical to patient stratification, additional analytes are evaluated for a patient stratification panel. These include the following.

Monocyte/macrophage and neutrophil activation markers: A study of smokers and "never-smokers" concluded that "healthy" smoking men with near normal FEV1 show signs of inflammation in the lower airways that are related to a decrease in DLCO and to emphysematous lesions on high resolution CT. As compared to never-smokers, smokers had higher blood levels of myeloperoxidase (MPO), human neutrophil lipocalin (HNL), eosinophil cationic protein (ECP), and lysozyme, higher levels of MPO, interleukin-8 (IL-8), and HNL in bronchial lavage (BL), and higher levels of IL-8, HNL, and interleukin-1α (IL-1α) in bronchoalveolar lavage (BAL). Smokers also had lower levels of Clara cell protein 16 (CC-16, an abundant component of airway secretions) in blood. HNL in BL and BAL showed strong correlation to other inflammatory markers, including MPO, IL-8, and IL-1α. The observed inflammation appeared to be the result of both monocyte/macrophage and neutrophil activation. In further studies, MIP-1α and HCC1 are used as potential markers.

Bacterial and viral antigens/antibodies: Studies in COPD patients have demonstrated that significant changes in antibody titers to putative pathogens can occur in the absence of symptoms, i.e., during periods of disease quiescence (Smith et al. (1976) *Lancet* 1:1253-1255) and during exacerbations even when sputum cultures were negative for the bacterium being studied (Reichek et al. (1970) *Am. Rev. Respir. Dis.* 101:238-244). Viral antigens and antibodies (e.g., RSV (Wilkinson et. al. (2006) *Am. J. Respir. Crit. Care Med.* 173: 871-876) also can be detected in the blood of patients prior to and during exacerbations. It is possible that plasma profiling will provide some rapid insight into treatment of exacerbations.

Once an antibody array is validated, an algorithm is designed for application of multiple biomarkers from sera, plasma, bronchiolar lavage, or sputum to diagnosis, prognosis, and patient stratification for clinical trials. Similarly, such panels are used for monitoring the treatment of COPD patients by identification of pharmacodynamic markers.

Example 4

A Method for Evaluating the Potential Side-Effect Profile of a Chemical Entity

Figure 28:
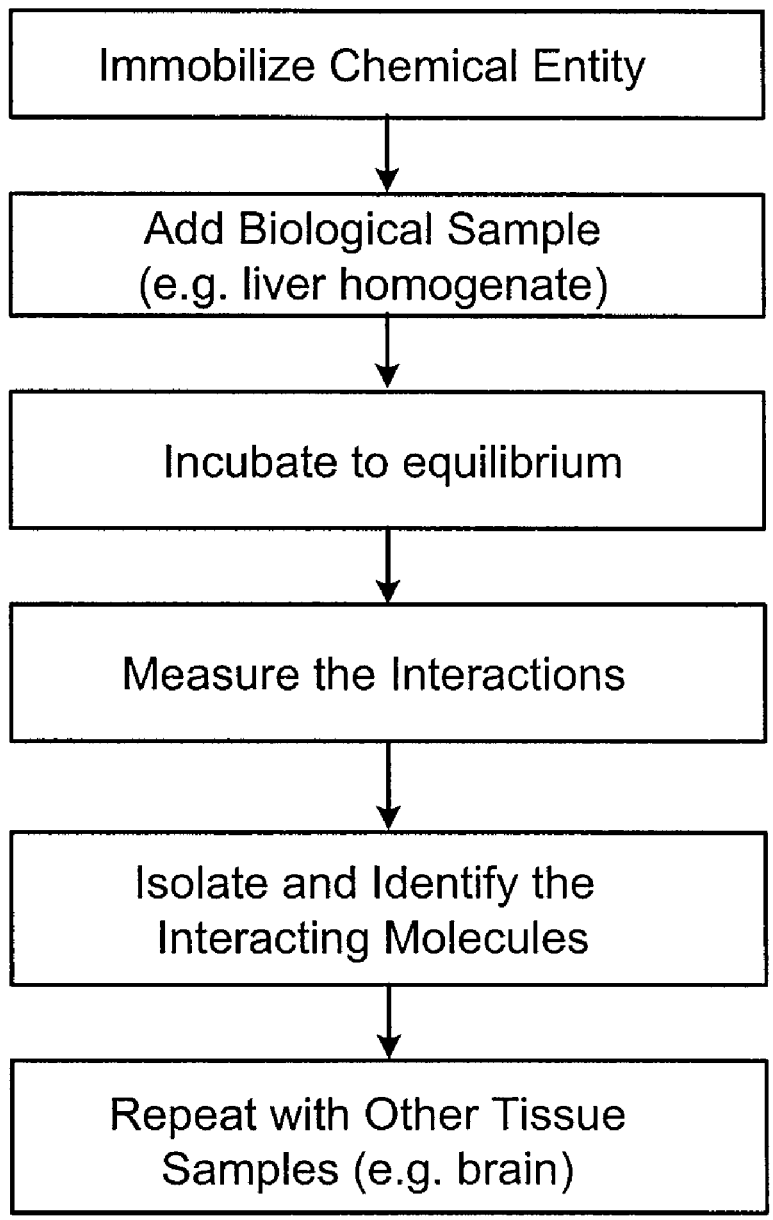
FIG. 28 is a flow diagram for a process wherein the side-effect profile of a chemical entity can be determined using a Molecular Interaction Measurement System (MIMS, PHB Labs, Durham, N.C.).

A chemical entity (compound) is immobilized on a surface directly or indirectly. A biological sample from a human or other animal is added to the surface to measure the interaction of the chemical entity (compound) with any particular biological molecules, including but not limited to polypeptides, DNA, RNA, lipids, and carbohydrates. The above biological samples are prepared from any and all organs, tissues, or biological fluids of human or other animals in which a side effect to the chemical entity is to be evaluated. In particular, the above surface on which the chemical entity is immobilized is part of a label-free system such as PHB's MIMS, which is used to detect interactions of the chemical entity with biological molecules. FIG. 28 depicts the scheme of such an iterative evaluation process.

A potential side-effect of the chemical entity are identified based on interactions of the chemical entity with biological molecules. After binding to the chemical entity, molecules can be eluted (e.g., with high salt, urea, or detergent) and further characterized using mass spectrometry or any other appropriate biochemical tests. By applying this method sequentially to a series of different tissue and body fluids, a potential toxicity profile is generated for a compound very early in the drug development process. This procedure can result in development of highly specific and valuable information. For example, if there is strong binding of a chemical compound to a protein from a heart muscle sample using the above process, it is an indication that this chemical entity may have an effect on the heart. If elution and purification of proteins bound to the chemical entity reveals the presence of, for example, myosin binding protein C (MyBP-C, one of the major sarcomeric proteins involved in the pathophysiology of familial hypertrophic cardiomyopathy), then insight is gained into the potential mechanism.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A process for diagnosing a human subject as having or not having depression, comprising:
    (a) obtaining a measured level for each of brain-derived neurotrophic factor (BDNF), alpha-2-macroglobulin (A2M), and interleukin-13 (IL-13) in a blood or a urine sample from the subject;
    (b) comparing the measured levels with control levels of BDNF, A2M, and IL-13 in blood or urine samples, respectively, from normal human subjects who do not have depression; and
    (c) diagnosing the subject as having depression if (i) the measured levels of BDNF and IL-13 are lower than the control levels for BDNF and IL-13 and (ii) the measured level of A2M is higher than the control level for A2M, or diagnosing the subject as not having depression if (i) the measured levels of BDNF and IL-13 are not lower than the control levels for BDNF and IL-1 3 and (ii) the measured level of A2M is not higher than the control level for A2M.

2. The process of claim 1, wherein said depression is a major depression disorder.

3. The process of claim 1, wherein said blood sample is whole blood.

4. The process of claim 1, wherein said blood sample is serum.

5. The process of claim 1, wherein said blood sample is plasma.

* * * * *